United States Patent
Freiburg et al.

(10) Patent No.: US 11,191,521 B2
(45) Date of Patent: *Dec. 7, 2021

(54) ACOUSTIC SIGNAL TRANSMISSION COUPLANTS AND COUPLING MEDIUMS

(71) Applicant: Decision Sciences Medical Company, LLC, Poway, CA (US)

(72) Inventors: Evan Freiburg, San Diego, CA (US); Dustin Kruse, Grand Island, NY (US)

(73) Assignee: Decision Sciences Medical Company, LLC, Poway, CA (US)

( * ) Notice: Subject to any disclaimer, the term of this patent is extended or adjusted under 35 U.S.C. 154(b) by 234 days.

This patent is subject to a terminal disclaimer.

(21) Appl. No.: 16/294,847

(22) Filed: Mar. 6, 2019

(65) Prior Publication Data
US 2019/0200957 A1    Jul. 4, 2019

Related U.S. Application Data

(63) Continuation of application No. 15/053,502, filed on Feb. 25, 2016, now Pat. No. 10,743,838.
(Continued)

(51) Int. Cl.
*A61B 8/00*       (2006.01)
*G01S 15/89*     (2006.01)
(Continued)

(52) U.S. Cl.
CPC .............. *A61B 8/4281* (2013.01); *A61B 8/14* (2013.01); *A61B 8/4209* (2013.01); *A61B 8/44* (2013.01);
(Continued)

(58) Field of Classification Search
CPC ....... A61B 8/4281; A61B 8/14; A61B 8/4209; A61B 8/4477; A61B 8/44; A61B 8/4483;
(Continued)

(56) References Cited

U.S. PATENT DOCUMENTS 4,105,018 A    8/1978    Greenleaf et al.
4,110,755 A    8/1978    Zottl
(Continued)

FOREIGN PATENT DOCUMENTS

CA    2427186 A1    5/2001
CA    2852801 A1    5/2013
(Continued)

OTHER PUBLICATIONS

International Search Report and Written Opinion dated Jul. 16, 2020 for International App. PCT/US20/29564 filed Apr. 23, 2020, 11 pages.
(Continued)

*Primary Examiner* — Sean D Mattson
(74) *Attorney, Agent, or Firm* — Perkins Coie LLP

(57) ABSTRACT

Devices, systems, and methods are disclosed for use in tomographic ultrasound imaging, large aperture ultrasound imaging and therapeutic ultrasound that provide for coupling acoustic signal transducers to body structures for transmitting and receiving acoustic signals. The acoustic signal transmission couplants can conform to the receiving medium (e.g., skin) of the subject such that there is an acoustic impedance matching between the receiving medium and the transducer. In one aspect, an acoustic coupling medium includes a hydrogel including polymerizable material that form a network structured to entrap an aqueous fluid inside the hydrogel. The hydrogel is structured to conform to the receiving body, and the acoustic coupling medium is operable to conduct acoustic signals between acoustic signal transducer elements and a receiving medium when the hydrogel is in contact with the receiving body such that there is an acoustic impedance matching between the receiving medium and the acoustic signal transducer elements.

19 Claims, 19 Drawing Sheets

Related U.S. Application Data

(60) Provisional application No. 62/120,839, filed on Feb. 25, 2015, provisional application No. 62/174,999, filed on Jun. 12, 2015.

(51) Int. Cl.

| | | |
|---|---|---|
| *G01S 7/52* | (2006.01) | |
| *A61B 8/14* | (2006.01) | |
| *A61B 17/225* | (2006.01) | |
| *A61B 8/08* | (2006.01) | |
| *A61N 7/00* | (2006.01) | |

(52) U.S. Cl.
CPC ........ *A61B 8/4477* (2013.01); *A61B 17/2251* (2013.01); *G01S 7/52079* (2013.01); *G01S 15/892* (2013.01); *G01S 15/8922* (2013.01); *A61B 8/0808* (2013.01); *A61B 8/4483* (2013.01); *A61B 8/467* (2013.01); *A61B 2017/2253* (2013.01); *A61N 7/00* (2013.01); *A61N 2007/0078* (2013.01)

(58) Field of Classification Search
CPC ... A61B 8/0808; A61B 8/467; A61B 17/2251; A61B 2017/2253; G01S 15/892; G01S 15/8922; G01S 7/52079; A61N 2007/0078; A61N 7/00; G10K 11/162–168
See application file for complete search history.

(56) References Cited

U.S. PATENT DOCUMENTS

| | | |
|---|---|---|
| 4,159,462 A | 6/1979 | Rocha et al. |
| 4,277,367 A | 7/1981 | Madsen et al. |
| 4,437,468 A | 3/1984 | Sorenson |
| 4,463,608 A | 8/1984 | Takeuchi et al. |
| 4,620,546 A | 11/1986 | Aida et al. |
| 4,821,206 A | 4/1989 | Arora |
| 4,830,015 A | 5/1989 | Okazaki |
| 4,888,746 A | 12/1989 | Wurster et al. |
| 5,005,418 A | 4/1991 | Anderson |
| 5,039,774 A | 8/1991 | Shikinami et al. |
| 5,181,513 A | 1/1993 | Touboul et al. |
| 5,241,964 A | 9/1993 | McQuilkin |
| 5,269,309 A | 12/1993 | Fort et al. |
| 5,284,143 A | 2/1994 | Rattner |
| 5,329,944 A | 7/1994 | Fabian et al. |
| 5,394,877 A * | 3/1995 | Orr .......................... A61B 5/25 600/459 |
| 5,417,218 A | 5/1995 | Spivey et al. |
| 5,445,144 A | 8/1995 | Wodicka et al. |
| 5,465,722 A | 11/1995 | Fort et al. |
| 5,522,878 A * | 6/1996 | Montecalvo ......... A61B 8/4281 600/437 |
| 5,533,510 A | 7/1996 | Koch, III et al. |
| 5,608,690 A | 3/1997 | Hossack et al. |
| 5,623,928 A | 4/1997 | Wright et al. |
| 5,682,886 A | 11/1997 | Delp et al. |
| 5,793,701 A | 8/1998 | Wright et al. |
| 5,800,356 A | 9/1998 | Criton et al. |
| 5,803,089 A | 9/1998 | Ferre et al. |
| 5,806,518 A | 9/1998 | Mittelstadt |
| 5,829,444 A | 11/1998 | Ferre et al. |
| 5,868,676 A | 2/1999 | McCabe et al. |
| 5,873,830 A | 2/1999 | Hossack et al. |
| 5,882,557 A | 3/1999 | Hayakawa et al. |
| 5,902,244 A | 5/1999 | Kobayashi et al. |
| 5,913,823 A | 6/1999 | Hedberg et al. |
| 5,967,980 A | 10/1999 | Ferre et al. |
| 6,016,285 A | 1/2000 | Wright et al. |
| 6,039,694 A * | 3/2000 | Larson ................. A61B 8/4281 600/459 |
| 6,045,507 A | 4/2000 | Muzilla et al. |
| 6,050,945 A | 4/2000 | Peterson et al. |
| 6,083,164 A | 7/2000 | Oppelt et al. |
| 6,106,464 A | 8/2000 | Bass et al. |
| 6,110,114 A | 8/2000 | Nock et al. |
| 6,113,544 A | 9/2000 | Mo |
| 6,123,669 A | 9/2000 | Kanda |
| 6,132,375 A | 10/2000 | Napolitano |
| 6,157,592 A | 12/2000 | Kriz et al. |
| 6,205,411 B1 | 3/2001 | DiGioia, III et al. |
| 6,231,834 B1 | 5/2001 | Unger et al. |
| 6,241,676 B1 | 6/2001 | Savord |
| 6,322,567 B1 | 11/2001 | Mittelstadt et al. |
| 6,338,765 B1 | 1/2002 | Statnikov |
| 6,340,363 B1 | 1/2002 | Bolger et al. |
| 6,341,231 B1 | 1/2002 | Ferre et al. |
| 6,402,707 B1 | 6/2002 | Ernst |
| 6,425,865 B1 | 7/2002 | Salcudean et al. |
| 6,436,045 B1 | 8/2002 | Rafter et al. |
| 6,445,943 B1 | 9/2002 | Ferre et al. |
| 6,508,766 B2 | 1/2003 | Sato et al. |
| 6,537,216 B1 | 3/2003 | Shifrin |
| 6,583,392 B2 | 6/2003 | Hershey et al. |
| 6,585,648 B1 | 7/2003 | Robinson |
| 6,620,101 B2 | 9/2003 | Azzam et al. |
| 6,626,916 B1 | 9/2003 | Yeung et al. |
| 6,652,461 B1 * | 11/2003 | Levkovitz ................ A61B 8/04 128/916 |
| 6,687,531 B1 | 2/2004 | Ferre et al. |
| 6,725,082 B2 | 4/2004 | Sati et al. |
| 6,736,780 B2 | 5/2004 | Song et al. |
| 6,757,582 B2 | 6/2004 | Brisson et al. |
| 6,785,571 B2 | 8/2004 | Glossop |
| 6,786,097 B2 | 9/2004 | Song et al. |
| 6,796,988 B2 | 9/2004 | Melkent et al. |
| 6,808,494 B2 | 10/2004 | Shifrin |
| 6,843,957 B2 | 1/2005 | Statnikov |
| 6,918,877 B2 | 7/2005 | Hossack et al. |
| 6,934,575 B2 | 8/2005 | Ferre et al. |
| 6,939,300 B2 | 9/2005 | Petersen et al. |
| 6,960,173 B2 | 11/2005 | Babaev |
| 7,004,906 B1 | 2/2006 | Guracar et al. |
| 7,066,886 B2 | 6/2006 | Song et al. |
| 7,207,939 B2 | 4/2007 | Husher |
| 7,226,456 B2 | 6/2007 | O'Neil et al. |
| 7,291,119 B1 | 11/2007 | de Guise et al. |
| 7,344,609 B2 | 3/2008 | Statnikov |
| 7,395,181 B2 | 7/2008 | Foxlin |
| 7,473,250 B2 | 1/2009 | Makin et al. |
| 7,532,201 B2 | 5/2009 | Quistgaard et al. |
| 7,542,790 B2 | 6/2009 | Jensen et al. |
| 7,566,304 B2 | 7/2009 | Nakamura et al. |
| 7,601,966 B2 | 10/2009 | Ben-Haim |
| 7,678,049 B2 | 3/2010 | Tsoref et al. |
| 7,719,515 B2 | 5/2010 | Fujiwara et al. |
| 7,719,689 B2 | 5/2010 | Lee et al. |
| 7,728,487 B2 | 6/2010 | Adachi et al. |
| 7,763,035 B2 | 7/2010 | Melkent et al. |
| 7,798,585 B2 | 9/2010 | Oguri |
| 7,806,823 B2 | 10/2010 | Sakai et al. |
| 7,826,889 B2 | 11/2010 | David et al. |
| 7,835,778 B2 | 11/2010 | Foley et al. |
| 7,835,784 B2 | 11/2010 | Mire et al. |
| 7,837,625 B2 | 11/2010 | Abe |
| 7,905,836 B2 | 3/2011 | Dan |
| 7,917,317 B2 | 3/2011 | McKeon |
| 7,938,777 B2 | 5/2011 | Amiot et al. |
| 7,938,778 B2 | 5/2011 | Sakai |
| 7,982,362 B2 | 7/2011 | Adachi et al. |
| 8,002,705 B1 | 8/2011 | Napolitano et al. |
| 8,038,616 B2 | 10/2011 | Angelsen et al. |
| 8,043,220 B2 | 10/2011 | Okada et al. |
| 8,103,461 B2 | 1/2012 | Glaser et al. |
| 8,105,339 B2 | 1/2012 | Melkent et al. |
| 8,126,533 B2 | 2/2012 | Lavallee |
| 8,147,409 B2 | 4/2012 | Shifrin |
| 8,152,726 B2 | 4/2012 | Amiot et al. |
| 8,165,658 B2 | 4/2012 | Waynik et al. |
| 8,241,217 B2 | 8/2012 | Chiang et al. |
| 8,251,908 B2 | 8/2012 | Vortman et al. |

(56) References Cited

U.S. PATENT DOCUMENTS

| | | |
|---|---|---|
| 8,253,578 B2 | 8/2012 | Watabe et al. |
| 8,311,611 B2 | 11/2012 | Csavoy et al. |
| 8,323,200 B2 | 12/2012 | Kunita |
| 8,372,070 B2 | 2/2013 | Tanaka et al. |
| 8,374,674 B2 | 2/2013 | Gertner |
| 8,409,099 B2 | 4/2013 | Vitek et al. |
| 8,409,103 B2 | 4/2013 | Grunwald et al. |
| 8,444,564 B2 | 5/2013 | Mahfouz et al. |
| 8,447,388 B2 | 5/2013 | Igarashi |
| 8,491,476 B2 | 7/2013 | Iwama et al. |
| 8,556,834 B2 | 10/2013 | Gertner |
| 8,565,860 B2 | 10/2013 | Kimchy et al. |
| 8,626,267 B2 | 1/2014 | Lavallee |
| 8,675,939 B2 | 3/2014 | Moctezuma de la Barrera |
| 8,771,188 B2 | 7/2014 | Schers et al. |
| 8,774,900 B2 | 7/2014 | Buly et al. |
| 8,814,810 B2 | 8/2014 | Roche et al. |
| 8,864,686 B2 | 10/2014 | Roche et al. |
| 8,880,152 B2 | 11/2014 | Lavallee |
| 8,909,325 B2 | 12/2014 | Kimchy et al. |
| 8,939,909 B2 | 1/2015 | Wegner |
| 9,060,794 B2 | 6/2015 | Kang et al. |
| 9,101,394 B2 | 8/2015 | Arata et al. |
| 9,174,065 B2 | 11/2015 | Gertner |
| 9,196,046 B2 | 11/2015 | Meyer |
| 9,220,571 B2 | 12/2015 | Lavallee |
| 9,244,169 B2 | 1/2016 | Fan et al. |
| 9,248,001 B2 | 2/2016 | Colombet et al. |
| 9,352,171 B2 | 5/2016 | Gertner |
| 9,387,276 B2 | 7/2016 | Sun et al. |
| 9,420,999 B2 | 8/2016 | Wegner |
| 9,572,548 B2 | 2/2017 | Moctezuma de la Barrera |
| 9,597,058 B2 | 3/2017 | Kanayama et al. |
| 9,844,359 B2 | 12/2017 | Wegner |
| 9,872,667 B2 | 1/2018 | Wegner |
| 10,085,722 B2 | 10/2018 | Wegner |
| 10,321,889 B2 | 6/2019 | Wegner |
| 10,426,429 B2 | 10/2019 | Kruse et al. |
| 2002/0068871 A1 | 6/2002 | Mendlein et al. |
| 2002/0099290 A1 | 7/2002 | Haddad |
| 2002/0122536 A1 | 9/2002 | Kerrien et al. |
| 2002/0188198 A1 | 12/2002 | Hong |
| 2002/0188229 A1 | 12/2002 | Ryaby et al. |
| 2003/0036702 A1 | 2/2003 | Davidsen |
| 2003/0125628 A1 | 7/2003 | Song et al. |
| 2003/0233045 A1* | 12/2003 | Vaezy ............... A61B 8/4281 600/437 |
| 2004/0066708 A1 | 4/2004 | Ogawa |
| 2004/0236223 A1 | 11/2004 | Barnes et al. |
| 2005/0101861 A1 | 5/2005 | Satoh |
| 2005/0101867 A1 | 5/2005 | Johnson et al. |
| 2005/0154302 A1 | 7/2005 | Sela et al. |
| 2005/0203399 A1 | 9/2005 | Vaezy |
| 2005/0215893 A1 | 9/2005 | Barnes et al. |
| 2006/0004290 A1 | 1/2006 | Smith et al. |
| 2006/0119223 A1 | 6/2006 | Ossmann |
| 2006/0173305 A1 | 8/2006 | Asafusa et al. |
| 2007/0066897 A1 | 3/2007 | Sekins et al. |
| 2007/0156050 A1 | 7/2007 | Barnes et al. |
| 2007/0226976 A1 | 10/2007 | Zipparo et al. |
| 2007/0239001 A1 | 10/2007 | Mehi et al. |
| 2007/0239002 A1 | 10/2007 | Alam |
| 2007/0265690 A1 | 11/2007 | Lichtenstein et al. |
| 2007/0276238 A1 | 11/2007 | Sudol |
| 2008/0110263 A1 | 5/2008 | Klessel et al. |
| 2008/0119737 A1 | 5/2008 | Urbano et al. |
| 2008/0200810 A1 | 8/2008 | Buchalter |
| 2008/0208055 A1 | 8/2008 | Bertram et al. |
| 2008/0281202 A1 | 11/2008 | Fraser et al. |
| 2008/0281237 A1* | 11/2008 | Slayton ............... A61B 8/4281 601/2 |
| 2009/0043206 A1 | 2/2009 | Towfiq et al. |
| 2009/0093737 A1* | 4/2009 | Chomas ............... A61N 7/02 601/2 |
| 2009/0124871 A1 | 5/2009 | Arshak et al. |
| 2009/0306497 A1 | 12/2009 | Manzke et al. |
| 2010/0029789 A1 | 2/2010 | Chen |
| 2010/0179425 A1 | 7/2010 | Zadicario |
| 2010/0204577 A1 | 8/2010 | Sekins et al. |
| 2010/0268072 A1 | 10/2010 | Hall et al. |
| 2010/0274139 A1 | 10/2010 | Fukukita et al. |
| 2010/0280379 A1 | 11/2010 | Satoh |
| 2010/0286518 A1 | 11/2010 | Lee et al. |
| 2010/0286527 A1 | 11/2010 | Cannon |
| 2011/0060226 A1 | 3/2011 | Yen et al. |
| 2011/0092862 A1 | 4/2011 | Chivers |
| 2011/0264012 A1 | 10/2011 | Lautzenhiser et al. |
| 2012/0029345 A1 | 2/2012 | Mahfouz et al. |
| 2012/0238875 A1 | 9/2012 | Savitsky et al. |
| 2012/0281507 A1 | 11/2012 | Rikoski |
| 2013/0060121 A1 | 3/2013 | Patwardhan et al. |
| 2013/0102875 A1 | 4/2013 | Dogra et al. |
| 2013/0123635 A1 | 5/2013 | Wegner |
| 2013/0144135 A1 | 6/2013 | Mahfouz et al. |
| 2013/0144166 A1 | 6/2013 | Specht et al. |
| 2013/0150863 A1 | 6/2013 | Baumgartner |
| 2013/0165005 A1 | 6/2013 | Berard-Andersen et al. |
| 2013/0218013 A1 | 8/2013 | Barthe et al. |
| 2014/0163377 A1 | 6/2014 | Kang et al. |
| 2014/0180116 A1 | 6/2014 | Lindekugel et al. |
| 2014/0353248 A1 | 12/2014 | Kuraray |
| 2015/0018682 A1 | 1/2015 | Schers et al. |
| 2015/0038613 A1 | 2/2015 | Sun et al. |
| 2015/0080725 A1 | 3/2015 | Wegner |
| 2015/0088040 A1 | 3/2015 | Barthe et al. |
| 2015/0133788 A1 | 5/2015 | Mauldin, Jr. et al. |
| 2015/0164467 A1 | 6/2015 | Suetoshi et al. |
| 2015/0182191 A1 | 7/2015 | Caluser et al. |
| 2015/0274805 A1 | 10/2015 | Annabi et al. |
| 2015/0313572 A1* | 11/2015 | Gerbaulet ............ A61B 8/0875 433/29 |
| 2016/0000409 A1 | 1/2016 | Bruder et al. |
| 2016/0100821 A1 | 4/2016 | Eggers et al. |
| 2016/0176128 A1* | 6/2016 | Zhao ............... C08J 3/075 424/9.1 |
| 2016/0270763 A1 | 9/2016 | Hayes et al. |
| 2016/0354520 A1 | 12/2016 | Sun et al. |
| 2017/0368333 A1 | 12/2017 | Loudin et al. |
| 2018/0126677 A1 | 5/2018 | Zhao et al. |
| 2018/0240366 A1 | 8/2018 | Felsinger et al. |
| 2019/0167234 A1 | 6/2019 | Wegner |
| 2020/0029931 A1 | 1/2020 | Kruse et al. |
| 2020/0029933 A1 | 1/2020 | Wegner |
| 2020/0337674 A1* | 10/2020 | Wegner ............... A61B 8/4422 |

FOREIGN PATENT DOCUMENTS

| | | |
|---|---|---|
| CN | 100354651 | 12/2007 |
| CN | 102258399 B | 11/2012 |
| CN | 104169739 | 11/2014 |
| EP | 0952461 A2 | 10/1999 |
| EP | 1707124 A2 | 4/2006 |
| EP | 1795917 A2 | 6/2007 |
| EP | 1854406 A1 | 11/2007 |
| EP | 1955668 A1 | 8/2008 |
| EP | 2033579 A1 | 3/2009 |
| GB | 2379392 | 3/2003 |
| GB | 2472066 A | 1/2011 |
| IL | 232148 A | 7/2019 |
| JP | 55051351 A | 4/1980 |
| JP | 58195550 A | 11/1983 |
| JP | 60048736 A | 3/1985 |
| JP | 62117535 A | 5/1987 |
| JP | 08038473 A | 2/1996 |
| JP | 2000041980 A | 2/2000 |
| JP | 2000166922 | 6/2000 |
| JP | 2000287988 | 10/2000 |
| JP | 2003190157 A | 7/2003 |
| JP | 2004147852 A | 5/2004 |
| JP | 2005152608 A | 6/2005 |
| JP | 2007152127 | 6/2007 |
| JP | 2010082425 A | 4/2010 |
| JP | 2011062531 | 3/2011 |
| JP | 2011177461 A | 9/2011 |

(56) References Cited

FOREIGN PATENT DOCUMENTS

| | | |
|---|---|---|
| JP | 2012002586 A | 1/2012 |
| JP | 2013056156 A | 3/2013 |
| JP | 2013520235 | 6/2013 |
| JP | 2013539715 | 10/2013 |
| JP | 2014533154 | 12/2014 |
| WO | 2002024094 A2 | 3/2002 |
| WO | 2007023477 A2 | 3/2007 |
| WO | 2009/009064 A1 | 1/2009 |
| WO | 2009/020617 A1 | 2/2009 |
| WO | 2009063421 A1 | 5/2009 |
| WO | 2013066821 A2 | 5/2013 |
| WO | 2013/103956 A1 | 7/2013 |
| WO | 2014/128593 A1 | 8/2014 |
| WO | 2014150780 A2 | 9/2014 |
| WO | 2014150961 A1 | 9/2014 |
| WO | 2014186904 A1 | 11/2014 |
| WO | 2015038554 A2 | 3/2015 |
| WO | 2016044830 A1 | 3/2016 |
| WO | 2016138257 A1 | 9/2016 |
| WO | 2016149427 A1 | 9/2016 |
| WO | 2017164902 | 9/2017 |

OTHER PUBLICATIONS

Australian Exam Report dated Nov. 1, 2019 for Australian Application No. 2016233279, filed on Mar. 16, 2016 (3 pages).
Australian Exam Report dated Oct. 18, 2019 for Australian Application No. 2016222637, filed on Feb. 25, 2016 (3 pages).
Callow, H.J., "Signal Processing for Synthetic Aperture Sonar Image Enhancement," Thesis for Ph.D. in Electrical and Electronic Engineering at the University of Canterbury, Christchurch, New Zealand, 273 pages, Apr. 2003.
Cao, Z. et al., "Fabrication and properties of thermosensitive organic/inorganic hybrid hydrogel thin films," Langmuir, American Chemical Society, vol. 24, No. 10, May 20, 2008, pp. 5543-5551.
Chiao, R., "Coded Excitation for Diagnostic Ultrasound: A System Developer's Perspective," *IEEE Transactions on Ultrasonics, Ferroelectrics, and Frequency Control*, 52(2): 160-170, Feb. 2005.
Choe, J.W., et al., "Volumetric real-time imaging using a CMUT ring array," IEEE Transactions on Ultrasonics, Ferroelectrics, and Frequency Control, 59(6):1201-1211, Jun. 2012.
Demi, L., et al., "In Vitro and In Vivo Tissue Harmonic Images Obtained With Parallel Transmit Beamforming by Means of Orthogonal Frequency Division Multiplexing," IEEE Transactions on Ultrasonics, Ferroelectrics, and Frequency Control, 62(1):230-235, Jan. 2015.
European Search Report dated Apr. 19, 2017 for European Application No. 14844538.0, filed on Sep. 9, 2014 (10 pages).
European Search Report dated Jun. 29, 2015 for European Application No. 12845256.2, filed on Oct. 29, 2012 (8 pages).
European Search Report dated Nov. 9, 2018 for European Application No. 16765701.4, filed on Mar. 16, 2016 (6 pages).
Extended European Search Report dated Feb. 15, 2019 for European Application No. 16765701.4, filed on Mar. 16, 2016 (14 pages).
Extended European Search Report dated Jul. 2, 2019 for European Application No. 16756353.5, filed on Feb. 25, 2016 (14 pages).
Extended European Search Report dated Jun. 18, 2019 for European Application No. 16854507.7, filed on Oct. 7, 2016 (11 pages).
Hunter, A.J., et al., "A Comparison of Fast Factorised Back-Projection and Wavenumber Algorithms for SAS Image Reconstruction," Proceedings of the World Congress on Ultrasonics, 4 pages, (2003).
International Search Report and Written Opinion dated Dec. 29, 2016 for International Application No. PCT/US2016/056159, filed on Oct. 7, 2016 (7 pages).
International Search Report and Written Opinion dated Mar. 3, 2015 for International Application No. PCT/US2014/054855, filed on Sep. 9, 2014 (11 pages).
International Search Report and Written Opinion dated May 15, 2013 for International Application No. PCT/US2012/062435, filed on Oct. 29, 2012 (9 pages).
Ito, T., et al., "Evaluation of Acoustic Imaging System Using Correlation Division in Synthetic Transmit Aperture with Multicarrier Signals," IEICE Transactions on Fundamentals of Electronics, Communications and Computer Sciences, E94-A(10):1907-1919, Oct. 2011.
Jensen, J.A., et al., "Synthetic Aperture Ultrasound Imaging," Ultrasonics, 44(Suppl 1):e5-e15, Dec. 2006.
Kundur, D., et al., "A Novel Blind Deconvolution Scheme for Image Restoration Using Recursive Filtering," IEEE Transactions on Signal Processing, 46(2):375-390, Feb. 1998.
Misaridis, T., "Use of Modulated Excitation Signals in Medical Ultrasound. Part I: Basic Concepts and Expected Benefits," *IEEE Transactions on Ultrasonics, Ferroelectrics, and Frequency Control*, 52(2):177-191, Feb. 2005.
Misaridis, T., "Use of Modulated Excitation Signals in Medical Ultrasound. Part II: Design and Performance for Medical Imaging Applications," *IEEE Transactions on Ultrasonics, Ferroelectrics, and Frequency Control*, 52(2):192-207, Feb. 2005.
Misaridis, T., "Use of Modulated Excitation Signals in Medical Ultrasound. Part III: High Frame Rate Imaging," *IEEE Transactions on Ultrasonics, Ferroelectrics, and Frequency Control*, 52(2):208-219, Feb. 2005.
O'Donnell, M., "Coded Excitation for Synthetic Aperture Ultrasound Imaging," *IEEE Transactions on Ultrasonics, Ferroelectrics, and Frequency Control*, 52(2):171-176, Feb. 2005.
Office Action dated Jul. 3, 2018 for Japanese Application No. 2017-187288, filed on Oct. 29, 2012 (6 pages).
Office Action dated Sep. 13, 2016 for Japanese Application No. 2014-539114, filed on Oct. 29, 2012 (4 pages).
Office Action dated Sep. 19, 2017 for Japanese Application No. 2016-542050, filed on Sep. 9, 2014 (15 pages).
Office Action dated Jun. 4, 2019 for Japanese Application No. 2017-187288, filed on Oct. 29, 2012 (3 pages).
Office Action dated Sep. 2, 2015 for Chinese Application No. 201280065031.4, filed on Oct. 29, 2012 (26 pages).
Prokop A F et al., "Polyacrylamide gel as an acoustic coupling medium for focused ultrasound therapy." Ultrasound in Medicine and Biol, New York, NY, US, vol. 29, No. 9, Sep. 1, 2003, pp. 1351-1358.
Rui Silva, S., et al., "2 Synthetic Aperture Techniques for Sonar Systems," Advances in Sonar Technology, edited by Sergio Rui Silva, publisher I-Tech Education and Publishing, ISBN 978-3-902613-48-6, pp. 15-42, Feb. 2009.
Singapore Exam Report dated Feb. 26, 2019 for Singapore Application No. 11201706953Y, filed on Feb. 25, 2016 (6 pages).
Singapore Written Opinion dated Jul. 10, 2017 for Singapore Application No. 11201601906P, filed on Sep. 9, 2014 (8 pages).
Singapore Written Opinion dated Jun. 21, 2018 for Singapore Application No. 11201707641P, filed on Mar. 16, 2016 (8 pages).
Zhu, S., et al., "SAS Autofocus Based on Phase Gradient Autofocus," IEEE 2011 Fourth International Workshop on Chaos-Fractals Theories and Applications (IWCFTA), pp. 298-301, Oct. 19-22, 2011.
Koch, A., et al., "An Ultrasound Tomography System With Polyvinyl Alcohol (PVA) Moldings for Coupling: In Vivo Results for 3-D Pulse-Echo Imaging of the Female Breast," IEEE Transactions on Ultrasonics, Ferroelectrics, and Frequency Control, 62(2):266-279, Feb. 2015.
International Search Report and Written Opinion dated Jul. 6, 2016 for International Application No. PCT/US2016/019554, filed on Feb. 25, 2016 (12 pages).
Examination Report dated Jun. 22, 2020 for Australian Application No. 2016334258, 4 pages.
Examination Report dated Dec. 20, 2019 for Europe Patent Application No. 14844538.0, filed on Sep. 9, 2014 (7 pages).
Office Action dated Jan. 13, 2020 for Chinese Application No. 201680028663.1, filed on Mar. 16, 2016 (17 pages).
Office Action dated Jan. 14, 2020 for Japanese Application No. 2017-563504, filed on Feb. 25, 2016 (14 pages).
Office Action dated Mar. 17, 2020 for Japanese Application No. 2018-145683, filed on Sep. 9, 2014 (4 pages).

(56) References Cited

OTHER PUBLICATIONS

Office Action dated Mar. 25, 2020 for Japanese Application No. 2016-542050, filed on Sep. 9, 2014 (4 pages).
Office Action dated Dec. 4, 2019 for Chinese Application No. 201680023999.9, filed on Feb. 25, 2016 (23 pages).
Office Action dated Feb. 25, 2020 for Japanese Application No. 2017-549178, filed on Mar. 16, 2016 (8 pages).
Singapore Written Opinion dated Mar. 11, 2020 for Singapore Application No. 11201707641P, filed on Mar. 16, 2016 (8 pages).
Office Action dated Jun. 5, 2018 for Chinese Patent Application No. 201480062224.3, filed on Sep. 9, 2014, 13 pages.
Office Action dated Jun. 18, 2019 for Japanese Patent Application No. 2018-145683, filed on Sep. 9, 2014, 12 pages.
Office Action dated Jun. 11, 2019 for Japanese Application No. 2016-542050, filed on Sep. 9, 2014 (15 pages).
Notification of Defects mailed Nov. 22, 2017 for Israel Patent Application No. 232148, filed on Oct. 29, 2012, 4 pages.
Second Office Action dated Jul. 20, 2016 for Chinese Patent Application No. 201280065031.4, filed on Oct. 29, 2012 (26 pages).
Examination Report dated Mar. 16, 2018 for European Application No. 12845256.2, filed on Oct. 29, 2012 (8 pages).
Examination Report dated Jul. 26, 2018 for Canada Patent Application No. 2,852,801, filed on Oct. 29, 2012, 4 pages.
First Examination Report dated Apr. 12, 2016 for Australian Patent Application No. 2012332817, filed on Oct. 29, 2012, 3 pages.
First Examination Report dated Nov. 21, 2018 for Australian Patent Application No. 2018203785, filed on Oct. 29, 2012, 2 pages.
European Search Report dated Jan. 25, 2019 for European Application No. 16756353.5, filed on Feb. 25, 2016 (14 pages).
Singapore Search Report dated Sep. 24, 2018 for Singapore Application No. 11201706953Y, filed on Feb. 25, 2016 (13 pages).
Office Action dated Sep. 23, 2020 in Israel Patent Application No. 254158, 3 pages.
Second Office Action dated Jul. 14, 2020 for Chinese Patent Application No. 201680023999.9, filed on Feb. 25, 2016, 41 pages, with English translation.
Office Action dated Aug. 30, 2020 for Israel Application No. 264906, filed on Oct. 29, 2012, with English translation, 10 pages.
Examination Report dated Jul. 19, 2021 for European Application No. 12845256.2, filed on Oct. 29, 2012 (8 pages).
Office Action dated Jun. 3, 2021 for Israel Application No. 258533, 7 pages, with English Translation.

\* cited by examiner

ACOUSTIC SIGNAL TRANSMISSION COUPLANTS AND COUPLING MEDIUMS

CROSS REFERENCE TO RELATED APPLICATIONS

This patent document is a continuation of and claims priority to U.S. patent application Ser. No. 15/053,502, filed on Feb. 25, 2016, which claims the benefit of priority of U.S. Provisional Patent Application No. 62/120,839, filed on Feb. 25, 2015, and U.S. Provisional Patent Application No. 62/174,999, filed on Jun. 12, 2015. The entire contents of the before-mentioned patent applications are incorporated by reference as part of the disclosure of this document.

TECHNICAL FIELD

This patent document relates to systems, devices, and processes for acoustic energy diagnostics and therapies.

BACKGROUND

Acoustic imaging is an imaging modality that employs the properties of sound waves traveling through a medium to render a visual image. High frequency acoustic imaging has been used as an imaging modality for decades in a variety of biomedical fields to view internal structures and functions of animals and humans. High frequency acoustic waves used in biomedical imaging may operate in different frequencies, e.g., between 1 and 20 MHz, or even higher frequencies, and are often termed ultrasound waves. Some factors, including inadequate spatial resolution and tissue differentiation, can lead to less than desirable image quality using conventional techniques of ultrasound imaging, which can limit its use for many clinical indications or applications.

SUMMARY

Techniques, systems, and devices are disclosed for coupling acoustic signal transducers to body structures for transmitting and receiving acoustic signals in ultrasound imaging, range-Doppler measurements, and therapies.

In one aspect, a couplant device of the disclosed technology for transmission of acoustic energy between transducers and a target includes a housing body structured to present an array of transducer elements on a curved section (e.g., curved lip) of the housing body (e.g., such as a semicircular or a circular portion that exposes the transducer elements of the array on a curved surface); and an acoustic coupling component including a hydrogel material (e.g., which may be at least partially contained in an outer lining). The acoustic coupling component is operable to conduct acoustic signals between a transducer element disposed in the housing body and a receiving medium (e.g., skin of a subject) in contact with the acoustic coupling component to propagate the acoustic signal toward a target volume, such that the acoustic coupling component is capable to conform to the target volume such that there is an acoustic impedance matching (e.g., very low attenuation) between the receiving medium and the transducer element.

The subject matter described in this patent document and attached appendices can be implemented in specific ways that provide one or more of the following features. For example, the couplant device can further include a flexible bracket coupled to and capable of moving with respect to the housing body, in which the flexible bracket secures the acoustic coupling component to the device. For example, the target volume includes a biological structure of a subject (e.g., an organ or tissue), and the receiving medium includes skin of the subject. In implementations of the couplant device, for example, the receiving medium can include hair on the exterior of the skin.

DETAILED DESCRIPTION

Figure 1A:
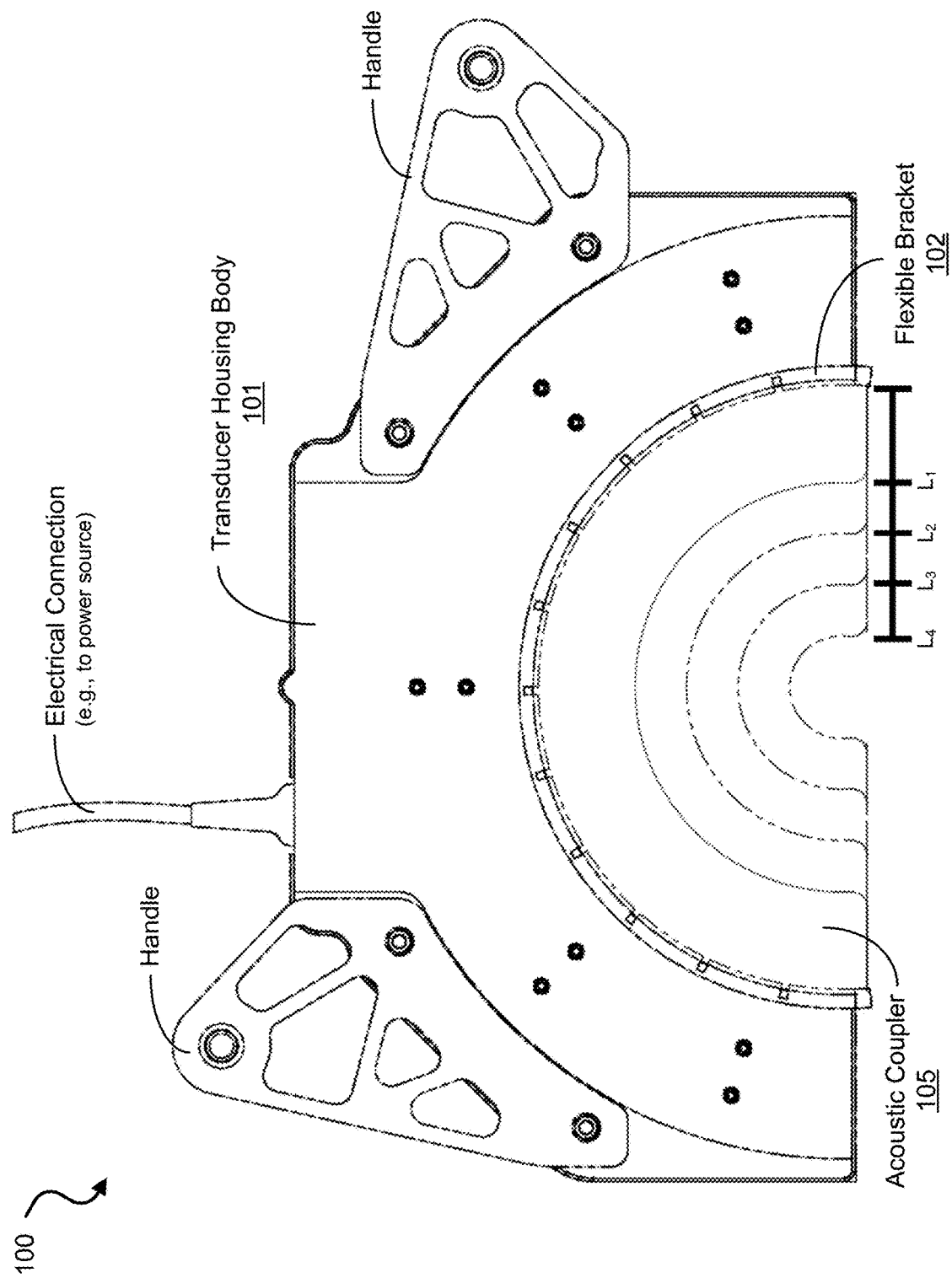
FIG. 1A shows a schematic diagram of an exemplary acoustic couplant device of the disclosed technology.

Acoustic imaging can be performed by emitting an acoustic waveform (e.g., pulse) within a physical elastic medium, such as a biological medium, including tissue. The acoustic waveform is transmitted from a transducer element (e.g., of an array of transducer elements) toward a target volume of interest (VOI). Propagation of the acoustic waveform in the medium toward the target volume can encounter structures that cause the acoustic waveform to become partly reflected from a boundary between two mediums (e.g., differing biological tissue structures) and partially transmitted. The reflection of the transmitted acoustic waveform can depend on the acoustic impedance difference between the two mediums (e.g., at the interface between two different biological tissue types). For example, some of the acoustic energy of the transmitted acoustic waveform can be scattered back to the transducer at the interface to be received, and processed to extract information, while the remainder may travel on and to the next medium. In some instances, scattering of the reflection may occur as the result of two or more impedances contained in the reflective medium acting as a scattering center. Additionally, for example, the acoustic energy can be refracted, diffracted, delayed, and/or attenuated based on the properties of the medium and/or the nature of the acoustic wave.

Acoustic wave speed and acoustic impedance differences can exist at the interface between the transducer and the medium to receive the acoustic waveform, e.g., referred to as the receiving medium, for propagation of the acoustic waveform toward the target volume, which can disrupt the transmission of the acoustic signal for imaging, range-Doppler measurement, or therapeutic applications. Acoustic impedance differences caused due to differing material properties (e.g., material density) of the two mediums and the acoustic wave velocity, such that a substantial amount of the emitted acoustic energy will be reflected at the interface rather than transferred in full across the interface. In typical acoustic (e.g., ultrasound) imaging or therapy applications, for example, a transmission gel is applied to the receiving medium (i.e., the skin of a subject) at the interface where the transducers will make contact to improve the transfer of the acoustic waveform(s) from the transducer to the body and the reception of the returned acoustic waveform(s) from the body back to the transducer. In such applications without the ultrasound gel, the interface may include air as a component of the medium between the receiving medium (e.g., living skin tissue) and the transducer, and an acoustic impedance mismatch in the transducer-to-air and the air-to-body discontinuity causes the scattering (e.g., reflection) of the emitted acoustic energy.

Despite relatively good success in reducing acoustic impedance difference at the interface, when applied, acoustic transmission gels may contain tiny packets of air that can disrupt the transmission of acoustic signals. Additionally, many patients complain of discomforts with the use of gels applied to their skin, e.g., such as temperature, stickiness, or other. More concerning, however, acoustic transmission gels can become contaminated during production or storage, which has led to infections within some patients. For subjects with hair on their skin at the location where the transducer is to be placed, these subjects typically must shave or otherwise remove the external hair which exasperates the trapping of air between the skin and gel.

For non-normal angles of incidence of the acoustic wave relative to the interface, the differences in the acoustic wave speed can result in refraction of the acoustic sound wave. Acoustic wave speed differences at the interface cause the propagation path of longitudinal acoustic waves to refract or change direction according to Snell's Law as a function of the angle of incidence and the acoustic wave speeds either side of the interface. Accumulations of infinitesimal amounts of refraction as the wave propagates in a heterogeneous material results in bending or curvature in the path of the acoustic wave.

As conventional ultrasound imaging assumes that acoustic waves travel in straight lines, refraction along the acoustic path causes degradation and distortion in the resulting image due the ambiguity it creates for the arrival time and location of an acoustic waveform in space for both transmission and reception. A material that matches the acoustic wave speed at the interface significantly reduces the effects of refraction, resulting in a clearer and less ambiguous image. Additionally, a material that has a homogeneous acoustic wave speed throughout will minimize the potential for curvature of acoustic wave paths inside the material.

Disclosed are techniques, systems, and devices for coupling acoustic signal transducers to body structures for transmitting and receiving acoustic signals in ultrasound imaging, range-Doppler measurements, and therapies. The disclosed acoustic signal transmission couplants can conform to the receiving medium (e.g., skin) of the subject such that there is an acoustic impedance matching between the receiving medium and the transducer.

Disclosed are also various embodiments of an acoustic coupling medium including a hydrogel formed from one or more polymerizable materials and capable of conforming or molding into specific three dimensional shapes for use in tomographic ultrasound imaging, large aperture ultrasound imaging, and therapeutic ultrasound.

In one embodiment, a couplant device of the disclosed technology for transmission of acoustic energy between transducers and a target includes a housing body including a curved surface on which an array of transducer elements may be disposed; and an acoustic coupling component including a hydrogel material, in which the acoustic coupling component is operable to conduct acoustic signals between a transducer element disposed in the housing body and a receiving medium (e.g., skin of a subject) in contact with the acoustic coupling component to propagate the acoustic signal toward a target volume, such that the acoustic coupling component is capable to conform to the receiving medium such that there is an acoustic impedance matching between the receiving medium and the transducer element. In some embodiments, the couplant device can further include a flexible bracket coupled to and capable of moving with respect to the housing body, in which the flexible bracket secures the acoustic coupling component to the device. For example, the target volume includes a biological structure of a subject (e.g., an organ or tissue), and the receiving medium includes skin of the subject. In implementations of the couplant device, for example, the receiving medium can include hair on the exterior of the skin.

Figure 1B:
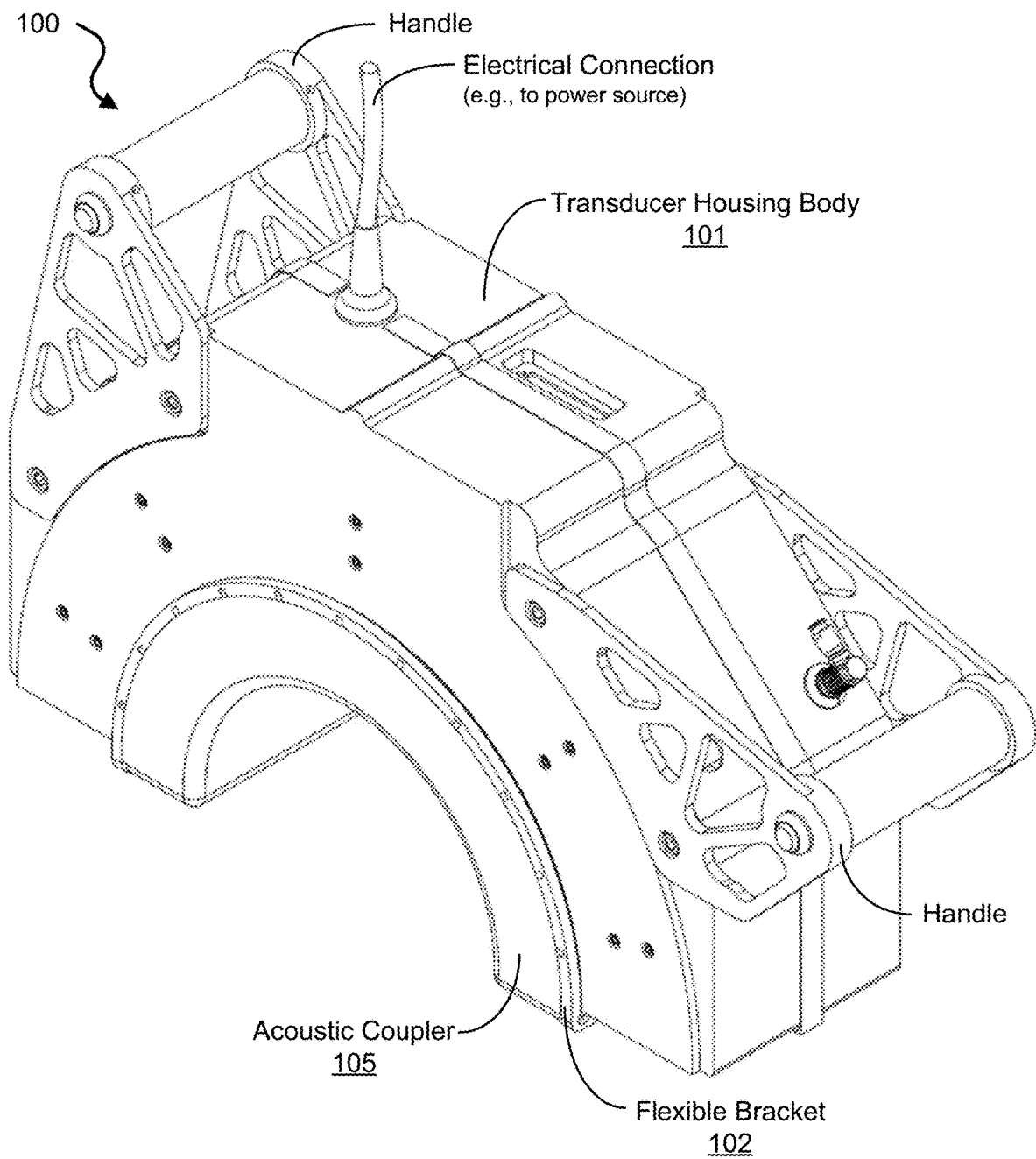
FIG. 1B shows a three dimensional view of an acoustic couplant device of the disclosed technology.
Figure 1C:
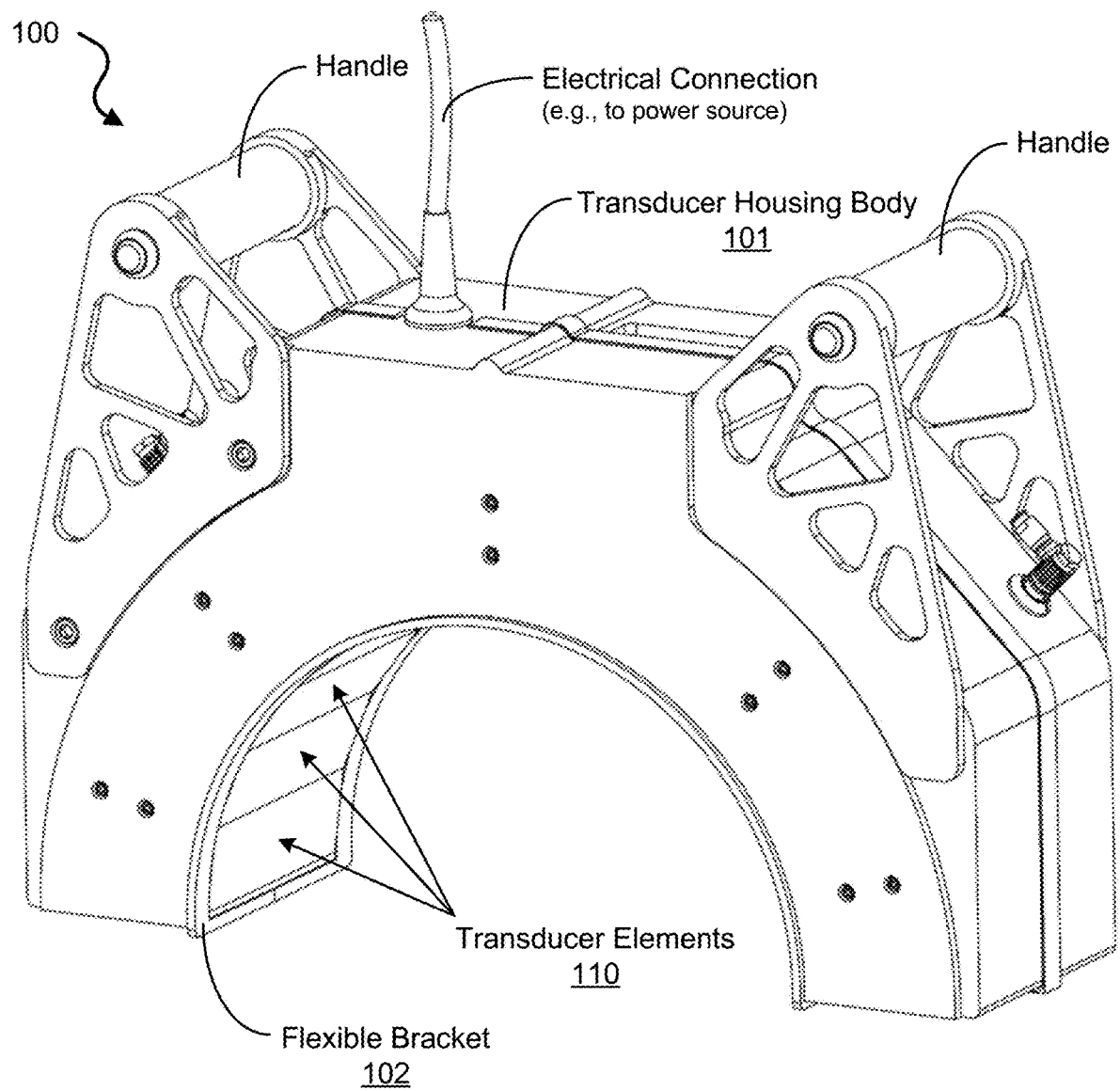
FIG. 1C shows another three dimensional view of an acoustic couplant device of the disclosed technology.

FIG. 1A shows a two dimensional side view schematic diagram and FIGS. 1B and 1C show three dimensional views of an acoustic couplant device 100 of the disclosed technology. The couplant device 100 includes a housing structure 101 to contain and position transducers for transmitting and receiving acoustic signals to/from a mass to which the acoustic couplant device 100 is applied. The housing structure 101 includes a curved section where transducer elements 110 of an acoustic transmit and/or receive transducer array are positioned, e.g., which is shown in FIG. 1C. The curved section of the housing structure 101 can be configured to various sizes and/or curvatures tailored to a particular body region or part where the couplant device 100 is to be applied in acoustic imaging, measurement, and/or therapy implementations. For example, the length, depth, and arc of the curved section of the housing structure 101 can be configured to make complete contact with a region of interest on an anatomical structure, e.g., such as a breast, arm, leg, neck, throat, knee joint, hip joint, ankle, waist, shoulder, or other anatomical structure of a human or animal (e.g., canine) subject to image or apply ultrasonic treatment to target volumes within such structures, such as splenic masses, cancerous or noncancerous tumors, legions, sprains, tears, bone outlines and other signs of damage or maladies. For example, the curved section of the housing structure 101 can include an aperture length in a range of a few centimeters to tens or hundreds of centimeters (e.g., such as an 18 cm baseline as depicted in FIG. 1A), an aperture depth in a range of a few centimeters to tens or hundreds of centimeters, and an arc or curvature of 1/(half or a few centimeters) to 1/(tens or hundreds of centimeters), e.g., $1/0.5$ cm$^{-1}$ to $1/18$ cm$^{-1}$. The couplant device 100 includes an acoustic coupler 105 attached to the housing structure 101 such that the acoustic coupler 105 is in contact with the external surface area of the transducer elements 110 disposed in the housing structure 101.

For example, the acoustic coupler 105 can be attached to the housing structure 101 by molding the hydrogel material against the curved section of the housing structure 101 to directly couple the acoustic coupler 105 and the transducer elements 110 at an interface. In such implementations, the housing structure 101 can include a securement mechanism (e.g., such as a clip) at various locations at the curved section to secure the molded acoustic coupler 105 to the housing structure 101, in which the securement mechanism is located on the housing structure 101 at locations away from the transducer elements 110 to not interfere with acoustic signal propagation transmitted and received by the transducer elements. In addition, or alternatively, for example, the housing structure 101 and/or the acoustic coupler 105 can include an adhesive portion to attach the molded acoustic coupler 105 to the curved section of the housing structure 101. In some implementations, for example, the adhesive portion can be configured as an adhesive layer attached to the receiving surface of the curved section of the housing structure 101 and/or an outer portion of the acoustic coupler 105. In some implementations, for example, the adhesive portion can include pretreatment of the outer portion areas of the hydrogel material of the acoustic coupler 105 (e.g., such as applying a low pH solution) to cause such areas to become naturally adhesive.

In some implementations, the acoustic coupler 105 includes a hydrogel material engineered to conduct acoustic signals between transducer elements 110 and a receiving medium (e.g., body region or part of the subject, e.g., such as the subject's midsection, head, or appendage) where the couplant device 100 is to be placed in contact to transmit and receive the acoustic signals propagating toward and from a target volume of interest in the subject. The acoustic coupler 105 is able to conform to the receiving medium to provide acoustic impedance matching between the transducer elements and the receiving medium (e.g., the skin of the subject, including body hair protruded from the skin).

The hydrogel material can be configured to have a selected thickness based on the size of the receiving body of the subject or object of the acoustic imaging, measurement, or therapy application. The diagram of FIG. 1A depicts the acoustic coupler 105 having various thicknesses L1, L2, L3, and L4 with respect to dimensions of the curved section of the housing structure 101. For example, in some embodiments, the L1 thickness can be 4 cm, the L2 thickness can be 6 cm, the L3 thickness can be 8 cm, and the L4 thickness can be 10 cm, e.g., in which the curved section of the housing structure 101 includes a semicircular geometry with a 12 cm radius. In some implementations, for example, the hydrogel material of the acoustic coupler 105 can include polyvinyl alcohol (PVA). In some implementations, for example, the hydrogel material can include polyacrylamide (PAA), which can include alginate. In some embodiments, for example, the acoustic coupler 105 can include an outer lining to encase at least some portions of the hydrogel. The exemplary outer lining can be formed over regions of the hydrogel that are in contact with the housing structure 101. In some implementations, for example, the exemplary outer lining can be configured to fully encase the hydrogel material to produce a pad. The hydrogel can flex, stretch and conform to any complex geometry surface to enable very low loss and a highly matched impedance path for efficient transmission of acoustic waveforms (e.g., ultrasonic waves) into tissue of the subject, e.g., including a human or any other animal. For example, the hydrogel can include a material structure that allows acoustic signal propagation with an attenuation factor of 0.1 dB/MHz$^2$·cm or less, an impedance of 1.5 MRayls or less, and a longitudinal speed of sound of 1540 m/s at 20° C. The acoustic coupler 105 is engineered to have a % elongation of 1000% or greater, a density of 1.00 g/cm$^3$±0.05 g/cm$^3$, a shear modulus of 1 MPa, and melting and freezing point of 70° C. and −5° C., respectively. For example, the hydrogel material can be at least 95% water and have a pH of ~7.0.

In some embodiments of the acoustic coupler 105, for example, one side of the hydrogel and/or outer lining is configured to have a tacky surface to contact the transducer elements 110 to promote adherence to the transducer face such that air or other substances are prohibited from becoming entrapped once the couplant device 100 is applied.

In some embodiments of the couplant device 100, for example, the housing structure 101 includes a flexible bracket 102 that attaches to the curved section of the housing structure 101 body. In some implementations, for example, the acoustic coupler 105 can be molded into the flexible bracket 102, which can also include the acoustic coupler 105 being adhesively attached (e.g., glued) to the flexible bracket 102 at portions of the acoustic coupler 105 away from acoustic signal propagation with the transducer elements. The flexible bracket 102 is structured to flex such that it can conform to the receiving body that it surrounds. For example, the flexible bracket 102 can include flexible materials, e.g., including, but not limited to, ABS plastic, polyurethane, nylon, and/or acetyl copolymer. FIGS. 2A-2D shows schematic diagrams of the acoustic coupler 105 attached to the flexible bracket 102.

Figure 2A:
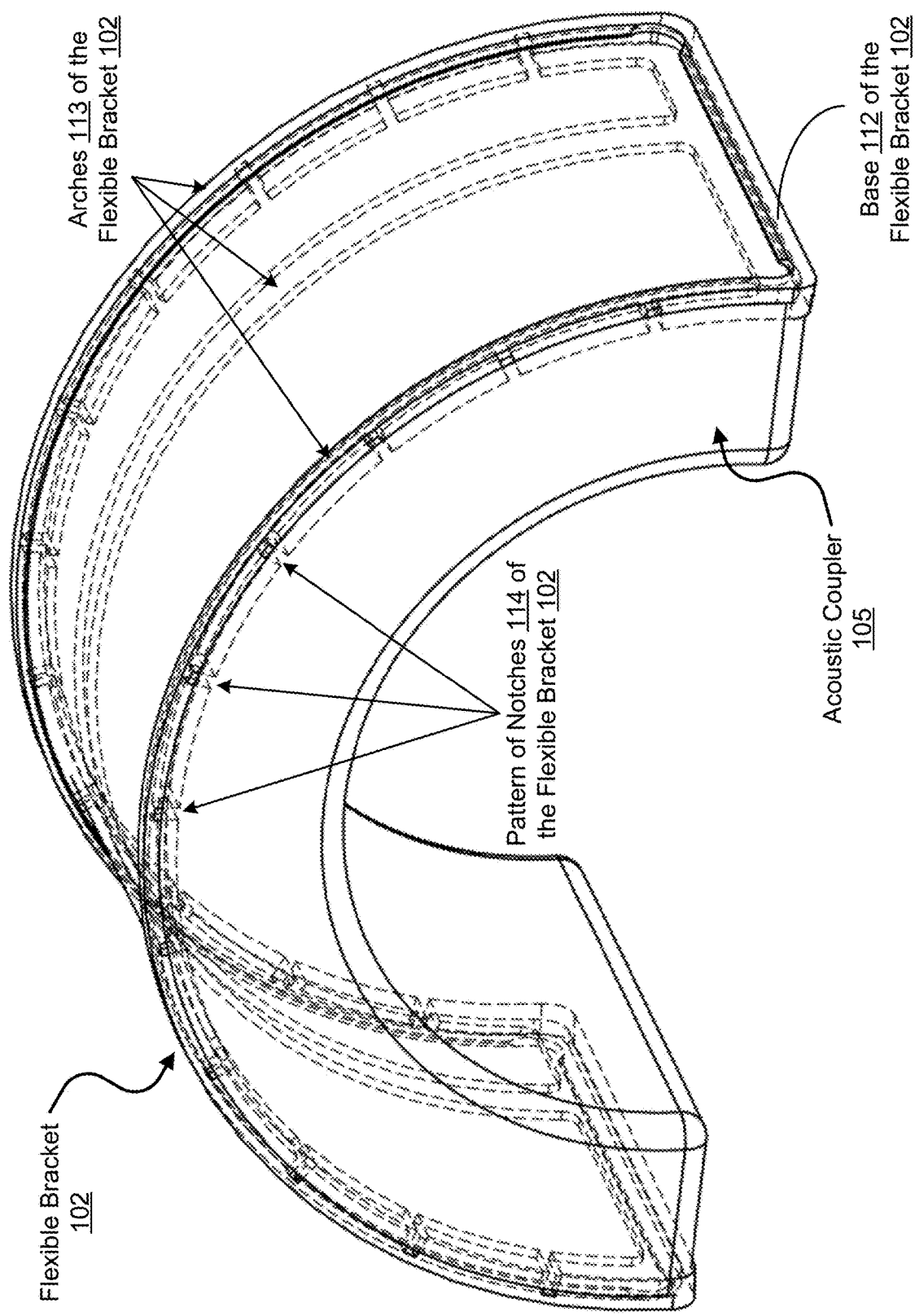
FIG. 2A shows a schematic diagram of an exemplary acoustic coupler of the disclosed technology attached to an exemplary flexible bracket to interface to an array of transducing elements.

FIG. 2A shows a three dimensional view schematic diagram of the acoustic coupler 105 attached to the flexible bracket 102. The flexible bracket 102 can be structured to include a base component 112 to attach to the ends of the acoustic coupler 105. For example, base component 112 can include clips to secure and/or adhere the acoustic coupler 105. In some embodiments, for example, the flexible bracket 102 can include one or more arch components 113 configured to a size and curvature to span across the curved section of the housing structure 101 and positioned at one or more respective locations on the base component 112 away from where the transducer elements 110 are positioned when the flexible bracket 102 is attached to the housing structure 101.

Figure 2B:
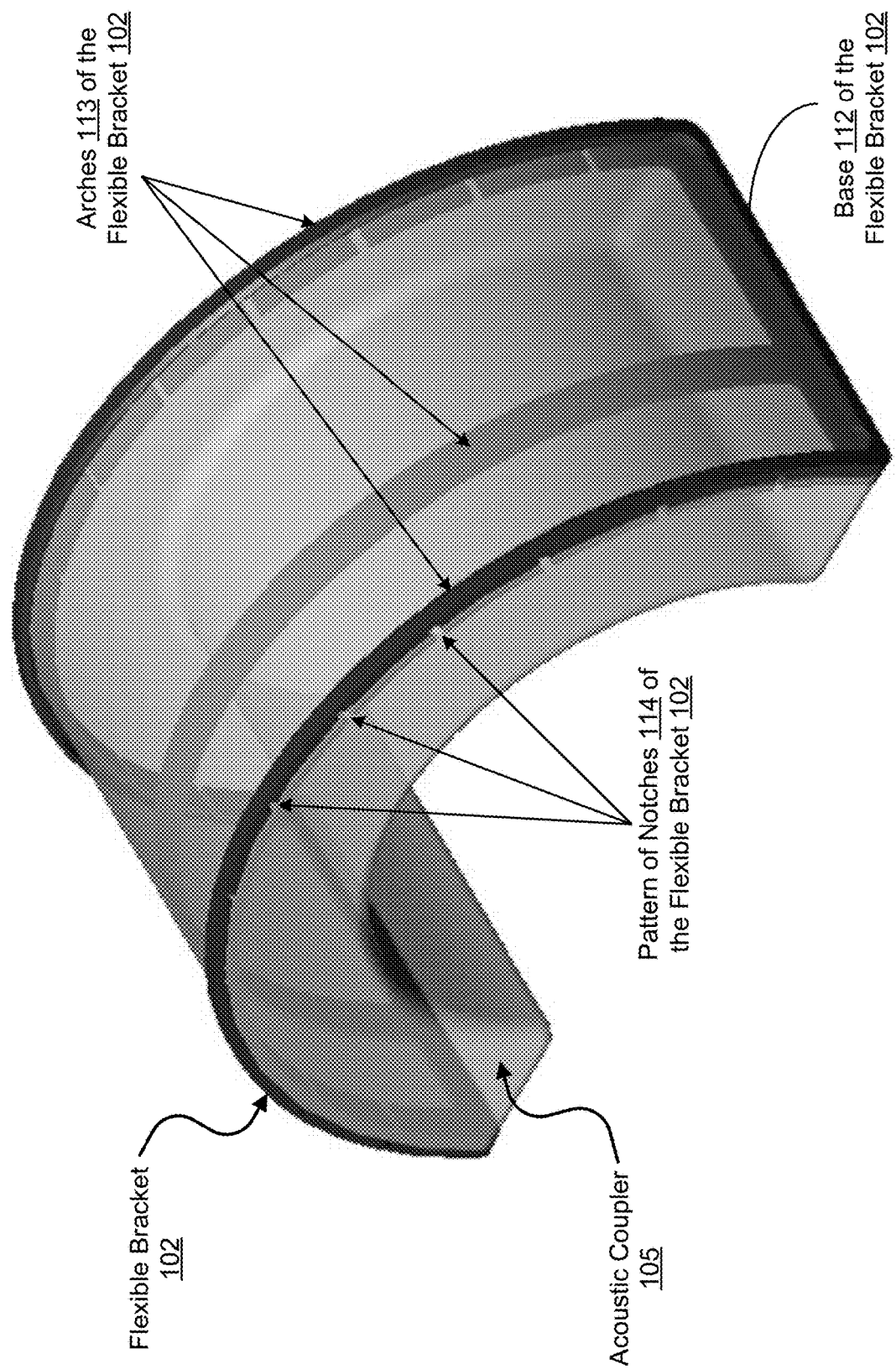
FIG. 2B shows a three dimensional view schematic diagram of an acoustic coupler attached to a flexible bracket in accordance with an exemplary embodiment.
Figure 2C:
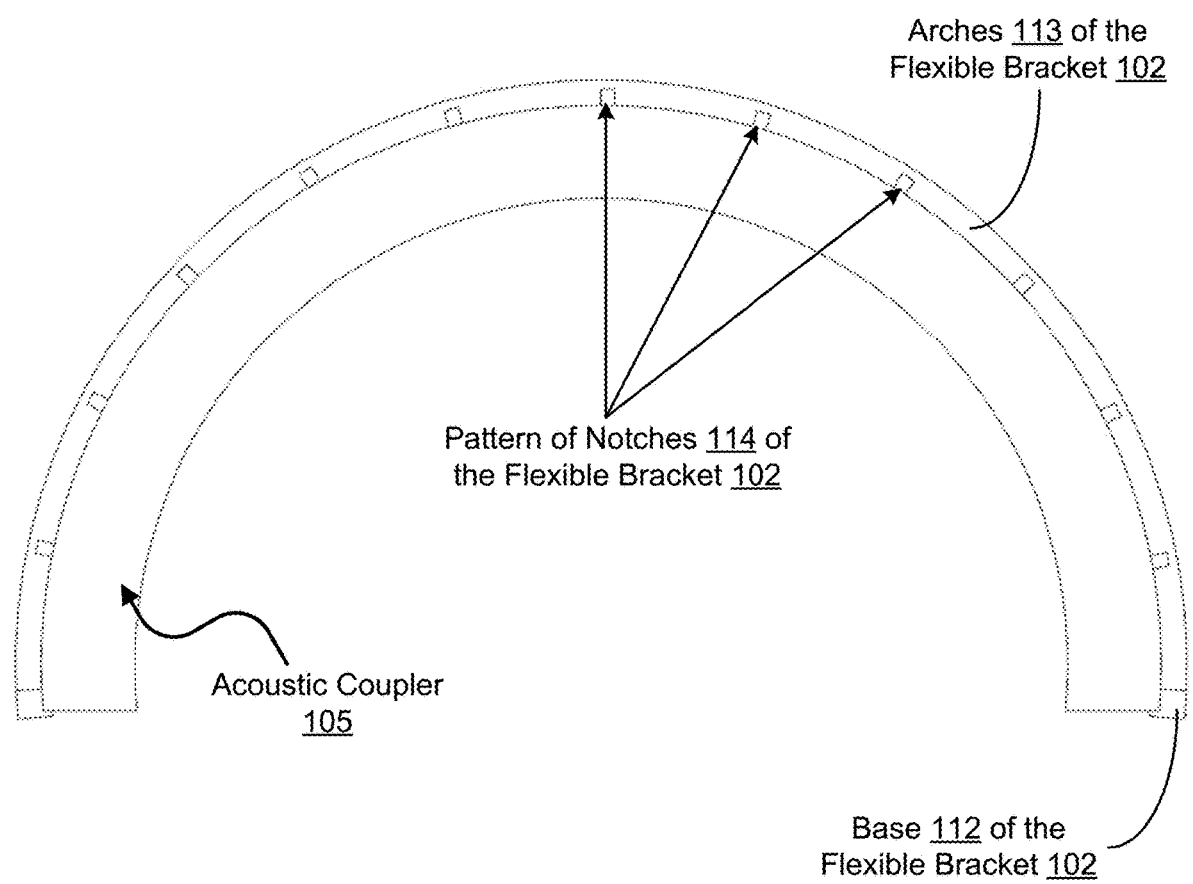
FIG. 2C shows a two dimensional side view schematic diagram of an acoustic coupler attached to a flexible bracket in accordance with an exemplary embodiment.

The flexible bracket 102 can be structured to have pattern of notches 114 on one side of the arch component(s) 113 to allow the flexible bracket 102 to bend easily without breaking. On the other side of the arch component(s) 113, the flexible bracket 102 can include an undercut lip with a chamfer so that when it's flexed into the shape of the array and pressed into position, the chamfered lip flexes over the lip on the curved section of the housing structure 101 and secures the flexible bracket 102, and thereby the acoustic coupler 105, in place. For example, the acoustic coupler 105 can be bonded or molded into the flexible bracket 102 when cross-linking of the hydrogel occurs. In some implementations, for example, the hydrogel of the acoustic coupler 105 can also be molded on the subject-facing side to smooth or curve the edges, e.g., which can allow the device 100 to contact and release from the subject easier. FIG. 2B shows a three dimensional view schematic diagram of the acoustic coupler 105 attached to the flexible bracket 102, and FIG. 2C shows a two dimensional side view schematic diagram of the acoustic coupler 105 attached to the flexible bracket 102.

Figure 2D:
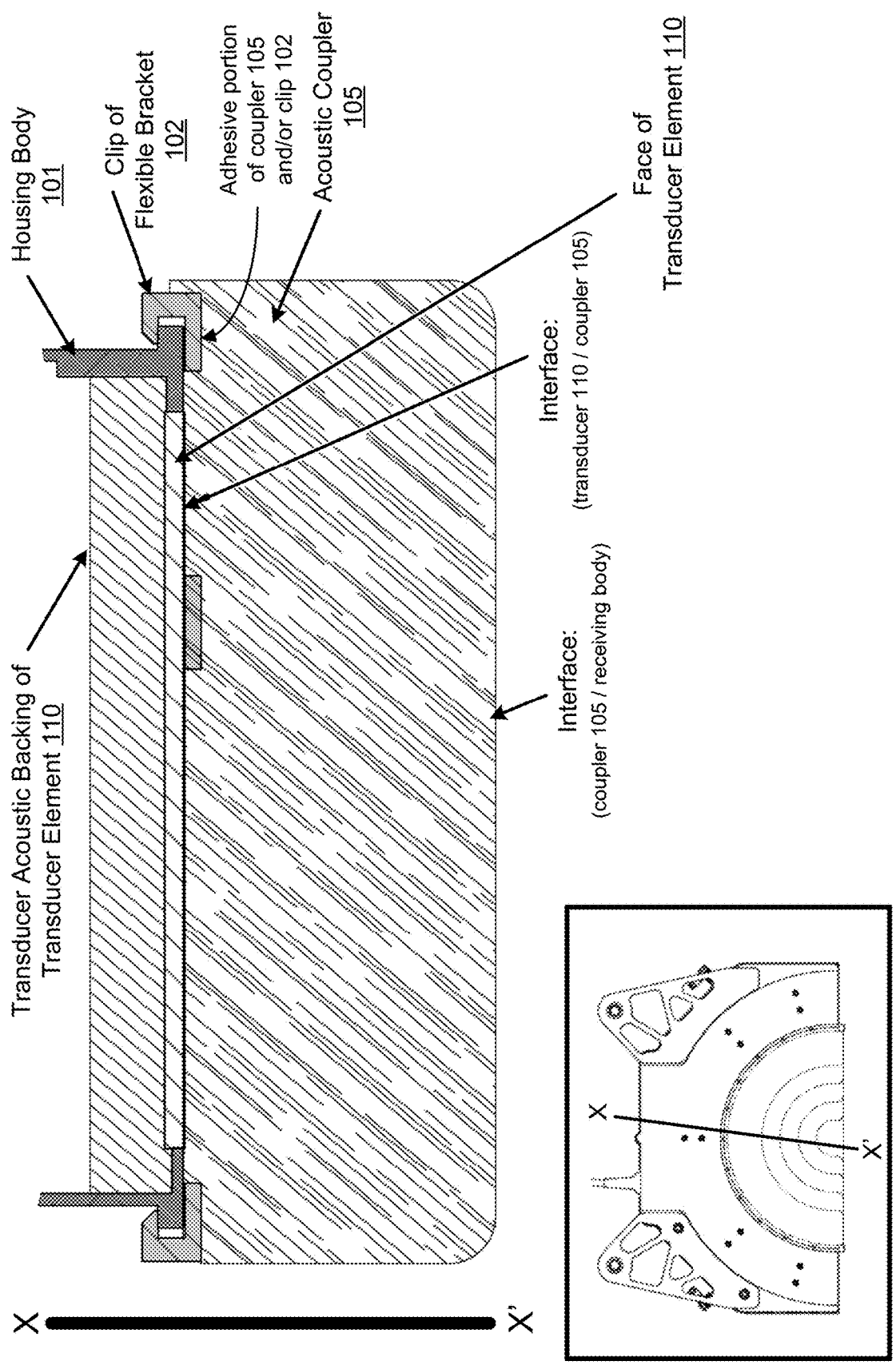
FIG. 2D shows a cross-sectional view schematic diagram of an acoustic coupler interfaced with a transducer element in accordance with an exemplary embodiment.

FIG. 2D shows a cross-sectional view schematic diagram of the acoustic coupler 105 interfaced with a transducer element 110 and attached to the housing structure 101 via the flexible bracket 102. As shown in this diagram, the acoustic coupler 105 conforms directly onto the face of the transducer element 110. In this example, the acoustic coupler 105 is attached to the clip components of the flexible bracket 102 by an adhesive on the external surface of the clips, e.g., to align in contact with the 'tacky regions' of the hydrogel and/or outer lining of the acoustic coupler 105. The clips attaches around the lip of the housing body 101 to provide direct contact between the acoustic coupler 105 and the face of the transducer element 110. As shown in the diagram, the transducer element 110 includes a transducer acoustic backing portion that interfaces with electrical communication elements for transduction of electrical to/from acoustic energy.

In some implementations of the couplant device 100, for example, the surface of the acoustic coupler 105 in contact with the subject can be lubricated so it can slide over the skin easily without trapping air bubbles for optimum acoustic transmission. Examples of such lubricants can include treating the side of the hydrogel material that is to be in contact with the subject with degassed and/or deionized water to render that portion of the hydrogel material highly lubricated.

Referring back to FIGS. 1A-1C, the housing structure 101 can include one or more handles to provide a place for a user to hold the couplant device 100 and/or move the couplant device 100 for positioning on the receiving body (e.g., a subject's torso, head, appendage, etc.) for an acoustic measurement or therapy. The housing structure 101 can include openings at various locations on the exterior of the housing structure 101 that provide access to the interior (e.g., including interior compartments) where electronic components including the transducer elements of the transducer array are located within the housing structure 101. For example, as depicted in FIG. 1A, an electrical cable or wires can be electrically connected to the electronics contained within the housing structure 101 for data communication and/or power supply. For example, the housing structure 101 can include compartments to secure signal conditioning and/or multiplexing circuitry in communication with the transducer elements 110, e.g., L0 transducer electronics, L1 A transducer electronics and multiplexing circuitry (e.g., multiplexing board type A), L1 B transducer electronics and multiplexing circuitry (e.g., multiplexing board type B), and/or L2 transducer level 2 MUX rigid flexible circuit card and flex mezzanine board. In some implementations, for example, the couplant device 110 includes a multiplexing unit contained in an interior compartment of the housing structure 101 and in communication with the transducer elements 110 to select one or more transducing elements 110 of the array to transmit individual acoustic waveforms, and to select one or more transducing elements 110 of the array to receive the returned acoustic waveforms. In some implementations of the couplant device, for example, the device 100 includes a data processing unit contained in a compartment in the housing structure 101 that includes signal conditioning circuitry to amplify the electrical signals transduced from the returned acoustic signals, and/or electrical signals to be transduced to the transmitted acoustic signals. In some embodiments of the exemplary data processing unit, for example, the data processing unit can include a processor and a memory to process and store data, respectively, which can be in communication with an input/output (I/O) unit to interface to transmit and receive data from an acoustic imaging and/or therapy system for controlling operations of the data processing unit of the device 100. In some implementations, for example, the data processing unit is in communication with the exemplary multiplexing unit.

As depicted in FIG. 1C, which shows the flexible bracket 102 attached to the transducer housing structure 101 without the acoustic coupler 105 presently attached, the transducer elements 110 can be arranged in a semicircular configuration to span along at least part of the curved section of the housing structure 101. The array of transducing elements 110 are presented on the curved geometry of this section of the housing structure 101 to be in direct contact with the acoustic coupler 105 to transmit and receive acoustic signals. In the exemplary embodiment shown, the transducer elements 110 are disposed on a lip of the curved section of the housing structure 101. Based on the flexibility, stretchability, and conformability of the acoustic coupler 105, the acoustic coupler 105 can remain in contact with the transducer elements 110 during application of the couplant device 100 as it is positioned and moved along the body structure of the subject. For example, the transducer elements 110 are arranged on the curved section (e.g., such as a semicircular ring, or a complete circular ring) of the housing structure 101. The flexible bracket 102 can include clips to attach to the lip 111 of the curved section. In some implementations, for example, the flexible bracket 102 can also include clips to secure the acoustic coupler 105 to the flexible bracket 102, which provides direct contact of the acoustic coupler 105 on to the face of the transducer elements 110 on the housing structure 101.

Figure 3A:
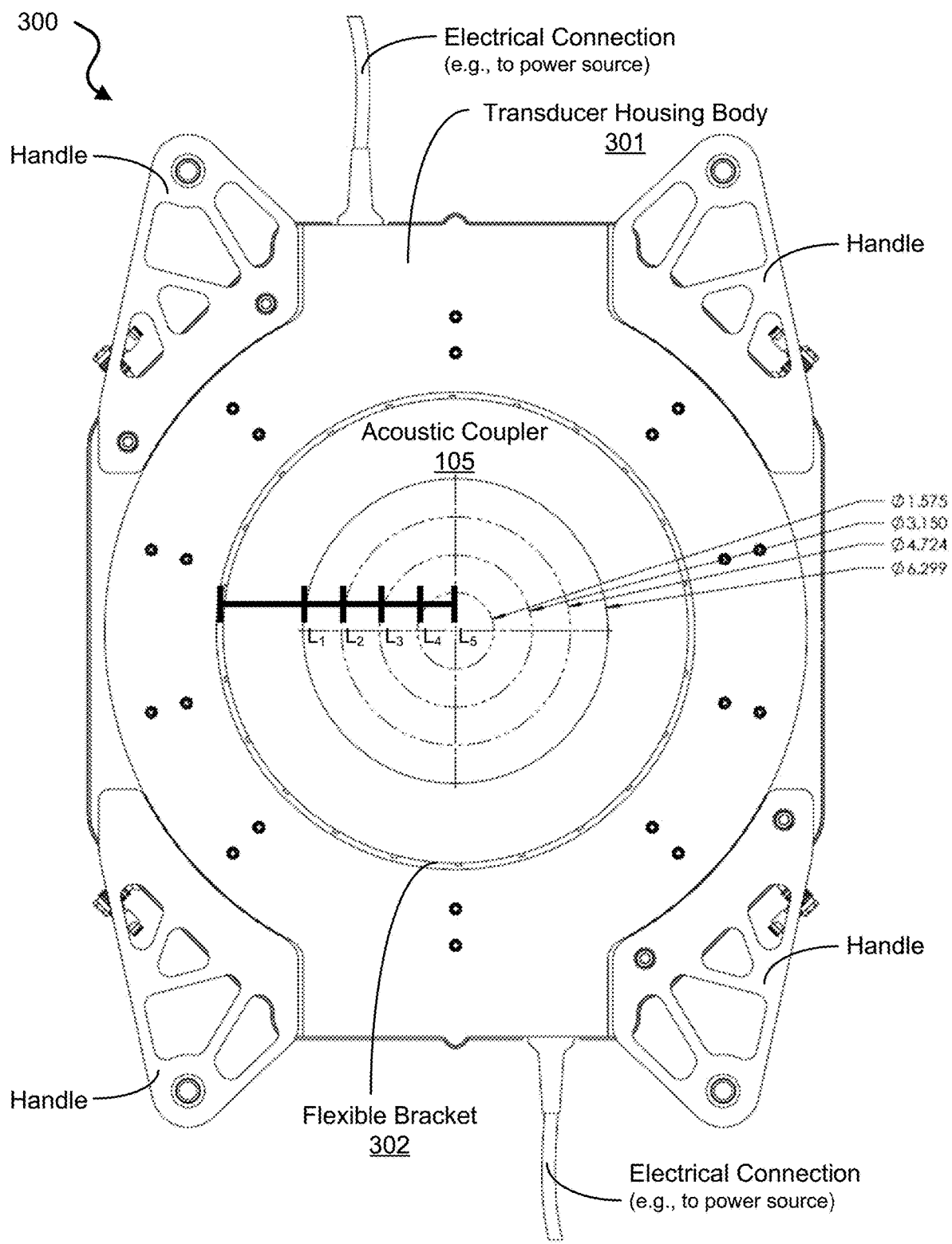
FIG. 3A shows a top view schematic diagram of an acoustic couplant device of the disclosed technology to provide a complete circular ring array of transducer elements.
Figure 3B:
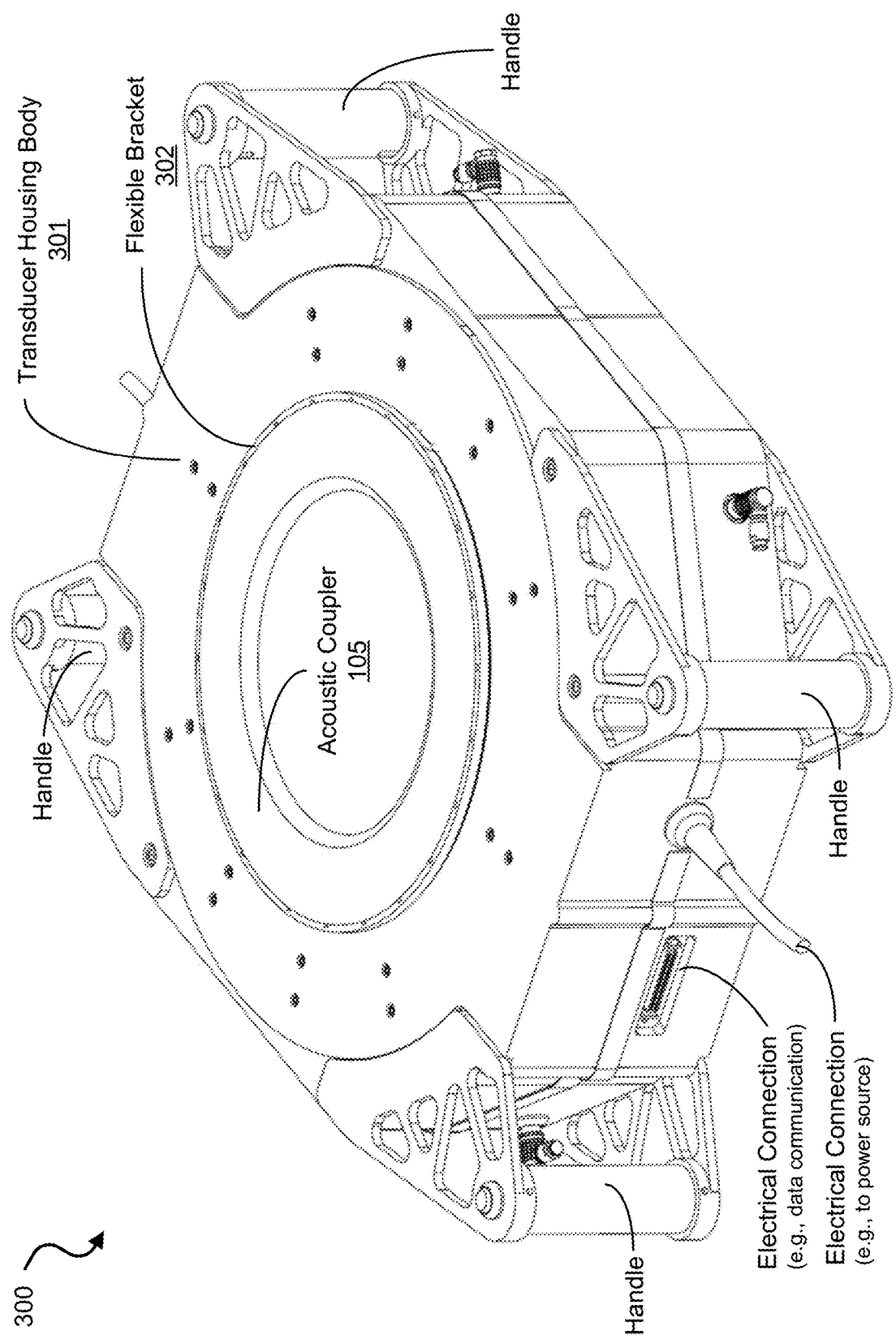
FIG. 3B shows a three dimensional schematic diagram of an acoustic couplant device of the disclosed technology to provide a complete circular ring array of transducer elements.

FIGS. 3A and 3B show a top view schematic diagram and three dimensional schematic diagram, respectively, of an acoustic couplant device 300 of the disclosed technology to provide a complete circular ring array of transducer elements 110. The couplant device 300 includes a housing structure 301 having a circular section to contain and position the transducer elements 110 for transmitting and receiving acoustic signals to/from a mass to which the acoustic couplant device 300 is applied. For example, the circular section of the housing structure 301 can include a circle geometry, elliptical geometry, or other curved geometry. The circular section of the housing structure 301 can be configured to various sizes and/or curvatures tailored to a particular body region or part where the couplant device 300 is to be applied in acoustic imaging, measurement, and/or therapy implementations. For example, the length, depth, and geometry of the circular section of the housing structure 301 can be configured to make complete contact, e.g., which can completely surround or enclose, with a region of interest on an anatomical structure of a subject, e.g., such as a breast, of a human or animal (e.g., canine) to image or apply ultrasonic treatment to target volumes within the structure. The couplant device 300 includes the acoustic coupler 105 attached to the housing structure 301 such that the acoustic coupler 105 is in contact with the external surface area of the transducer elements 110 disposed in the circular section of the housing structure 301.

The couplant device 300 an include a flexible bracket 302 to attach to the circular section of the housing structure 301 body to couple the acoustic coupler 105 to the transducer elements 110 housed in the housing structure 301. In some implementations, for example, the acoustic coupler 105 can be molded into the flexible bracket 302, which can include the acoustic coupler 105 being adhesively attached to the flexible bracket 302 at portions of the acoustic coupler 105 away from acoustic signal propagation with the transducer elements.

Figure 4:
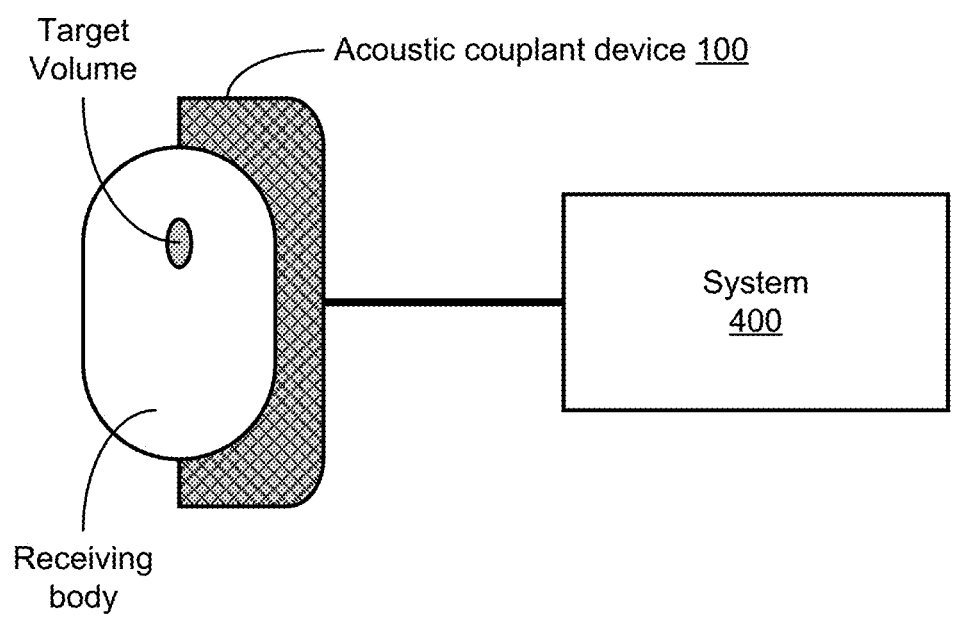
FIG. 4 shows a block diagram of an exemplary acoustic imaging and/or therapy system of the disclosed technology.

FIG. 4 shows a block diagram of an acoustic imaging system 400 in communication with the acoustic couplant device 100 for acoustic imaging, range-Doppler measurements, and/or therapeutic application of acoustic energy of a target volume in a receiving body (e.g., anatomical structure of a human or non-human animal subject) to which the acoustic couplant device 100 is applied. Examples of acoustic systems, devices, and methods for acoustic imaging, range-Doppler measurements, and therapies are described in U.S. Pat. No. 8,939,909, titled "Spread Spectrum Coded Waveforms in Ultrasound Imaging," and U.S. Patent Application Publication No. 2015/0080725, titled "Coherent Spread-Spectrum Coded Waveforms in Synthetic Aperture Image Formation," both of which are incorporated by reference in this patent document. In some implementations, such acoustic systems can generate, transmit, receive, and process arbitrary or coded acoustic waveforms that create a large, synthetic aperture. For example, coherent, spread-spectrum, instantaneous-wideband, coded waveforms can be produced in synthetic aperture ultrasound (SAU) applications using such acoustic systems, e.g., employing the disclosed acoustic coupling medium.

Referring to FIG. 4, the system 400 can include systems and/or devices described in the '909 patent and the '725 patent publication. The system 400 can be used to produce acoustic waveforms transduced by the device 100 (or the device 300) for transmission toward the target volume (and reception of returned acoustic waveforms), such that the acoustic waveforms have enhanced waveform properties that include a spread-spectrum, wide instantaneous bandwidth, coherency, pseudo-random noise characteristics, and frequency- and/or phase-coding. In some implementations, the system 400 can be used to produce acoustic waveforms across an expanded effective (synthetic) aperture using the device 100 (or the device 300) for transmission toward the target volume (and reception of returned acoustic waveforms), in which the acoustic waveforms have enhanced waveform properties including a spread-spectrum, wide instantaneous bandwidth, coherent, pseudo-random noise characteristics, and coding.

EXAMPLES

The following examples are illustrative of several embodiments of the present technology. Other exemplary embodiments of the present technology may be presented prior to the following listed examples, or after the following listed examples.

In one example of the present technology (example 1), a couplant device for transmission of acoustic energy between transducers and a target includes an array of transducer elements to transmit acoustic signals toward a target volume and to receive returned acoustic signals that return from at least part of the target volume; a housing body including a curved section on which the array of transducer elements are arranged; and an acoustic coupling component including a hydrogel material, the acoustic coupling component operable to conduct the acoustic signals between a transducer element disposed in the housing body and a receiving medium in contact with the acoustic coupling component to propagate the acoustic signals toward the target volume, in which the acoustic coupling component is capable to conform to the receiving medium and the transducer element such that there is an acoustic impedance matching between the receiving medium and the transducer element.

Example 2 includes the device of example 1, in which the device further includes a flexible bracket coupled to and capable of moving with respect to the housing body, in which the acoustic coupling component is attached to the flexible bracket.

Example 3 includes the device of example 1, in which the hydrogel material includes polyvinyl alcohol (PVA).

Example 4 includes the device of example 1, in which the hydrogel material includes polyacrylamide (PAA).

Example 5 includes the device of example 4, in which the hydrogel material includes alginate.

Example 6 includes the device of example 1, in which the acoustic coupling component includes an outer lining at least partially enclosing the hydrogel material.

Example 7 includes the device of example 1, in which the acoustic coupling component is operable to propagate the acoustic signals with an attenuation factor of 0.1 dB/MHz2·cm or less, or with an impedance of 1.5 MRayls or less.

Example 8 includes the device of example 1, in which the acoustic coupling component is capable to undergo a % elongation of 1000% or greater, or includes a shear modulus of 1 MPa.

Example 9 includes the device of example 1, in which the target volume includes a biological structure of a living subject and the receiving medium includes an anatomical structure of the living subject.

Example 10 includes the device of example 9, in which the curved section of the housing body includes a curvature to facilitate complete contact with the anatomical structure, such that the acoustic coupling component is in direct contact with skin of the anatomical structure.

Example 11 includes the device of example 10, in which the anatomical structure includes hair on the exterior of the skin.

Example 12 includes the device of example 9, in which the anatomical structure includes a breast, an arm, a leg, a neck including the throat, a knee joint, a hip joint, an ankle joint, an elbow joint, a shoulder joint, an abdomen, or a chest, or a head.

Example 13 includes the device of example 9, in which the biological structure includes a cancerous or noncancerous tumor, an internal legion, a connective tissue sprain, a tissue tear, or a bone.

Example 14 includes the device of example 9, in which the subject includes a human or a non-human animal.

Example 15 includes the device of example 1, in which the curved section of the housing body includes a semicircular geometry.

Example 16 includes the device of example 1, in which the curved section of the housing body includes a 360° circular geometry, and the array of transducer elements arranged along the 360° circular section of the housing body.

Example 17 includes the device of example 16, in which the 360° circular section of the housing body and the acoustic coupling component provide a curvature to facilitate complete contact around an anatomical structure of a living subject, and in which the device is operable to receive the returned acoustic signals from the target volume such that an acoustic imaging system in data communication with the device is able to produce a 360° image of the target volume.

Example 18 includes the device of example 1, in which the device further includes a multiplexing unit contained in an interior compartment of the housing body and in communication with the array of transducer elements to select one or more transducing elements of the array to transmit individual acoustic waveforms, and to select one or more transducing elements of the array to receive the returned acoustic waveforms.

In one example of the present technology (example 19), an acoustic waveform system includes a waveform generation unit, an acoustic signal transmission couplant, a multiplexing unit, and a controller unit. The waveform generation unit includes one or more waveform synthesizers coupled to a waveform generator, in which the waveform generation unit is operable to synthesize a composite waveform that includes a plurality of individual orthogonal coded waveforms corresponding to different frequency bands that are generated by the one or more waveform synthesizers according to waveform information provided by the waveform generator, in which the individual orthogonal coded waveforms are mutually orthogonal to each other and correspond to different frequency bands, such that each of the individual orthogonal coded waveforms includes a unique frequency with a corresponding phase. The acoustic signal transmission couplant includes a housing body including a curved section on which transducer elements are arranged; an array of transducer elements to transmit acoustic waveforms corresponding to the individual orthogonal coded waveforms toward a target volume and to receive returned acoustic waveforms that return from at least part of the target volume; and an acoustic coupling component including a hydrogel material, the acoustic coupling component operable to conduct the acoustic waveforms between a transducer element disposed on the housing body and a receiving medium in contact with the acoustic coupling component, in which the acoustic coupling component is capable to conform to the receiving medium and the transducer element such that there is an acoustic impedance matching between the receiving medium and the transducer element. The multiplexing unit is in communication with the array of transducer elements and operable to select one or more transducing elements of an array to transduce the individual orthogonal coded waveforms into the corresponding acoustic waveforms, and operable to select one or more transducing elements of the array to receive the returned acoustic waveforms. The controller unit, which is in communication with the waveform generation unit and the multiplexing unit, includes a processing unit to process the received returned acoustic waveforms to produce a data set including information of at least part of the target volume.

Example 20 includes the system of example 19, further including an array of analog to digital (A/D) converters to convert the received returned acoustic waveforms received by the array of transducer elements of the acoustic signal transmission couplant from analog format to digital format as a received composite waveform that includes information of at least part of the target volume.

Example 21 includes the system of example 19, further including a user interface unit in communication with the controller unit.

Example 22 includes the system of example 19, in which the produced data set includes an image of at least part of the target volume.

Example 23 includes the system of example 19, in which the acoustic signal transmission couplant includes a flexible bracket coupled to and capable of moving with respect to the housing body, in which the acoustic coupling component is attached to the flexible bracket.

Example 24 includes the system of example 23, in which the hydrogel material includes at least one of polyvinyl alcohol (PVA), polyacrylamide (PAA), or PAA with alginate.

Example 25 includes the system of example 19, in which the curved section of the housing body of the acoustic signal transmission couplant includes a semicircular geometry, or the curved section of the housing body of the acoustic signal transmission couplant includes a 360° circular geometry such that the array of transducer elements are arranged along the 360° circular section of the housing body.

Example 26 includes the system of example 25, in which the 360° circular section of the housing body and the acoustic coupling component provide a curvature to facilitate complete contact around an anatomical structure of a living subject, and in which the device is operable to receive the returned acoustic waveforms from the target volume such that the system is able to produce a 360° image of the target volume.

In one example of the present technology (example 27), a method of producing acoustic waveforms using an acoustic impedance matched couplant includes: synthesizing, in one or more waveform synthesizers, one or more composite waveforms to be transmitted toward a target, in which a composite waveform is formed of a plurality of individual orthogonal coded waveforms that are mutually orthogonal to each other and correspond to different frequency bands, such that each of the individual orthogonal coded waveforms includes a unique frequency with a corresponding phase; transmitting, from one or more transmitting positions relative to the target using an array of transducing elements of an acoustic signal transmission couplant, one or more composite acoustic waveforms that includes a plurality of acoustic waveforms, in which the transmitting includes selecting one or more of the transducing elements of the array to transduce the plurality of individual orthogonal coded waveforms of the respective one or more composite waveforms into the plurality of corresponding acoustic waveforms of the respective one or more composite acoustic waveforms; and receiving, at one or more receiving positions relative to the target, returned acoustic waveforms that are returned from at least part of the target corresponding to the transmitted acoustic waveforms, in which the receiving includes selecting at least some of the transducing elements of the array to receive the returned acoustic waveforms, in which the transmitting positions and the receiving positions each include (i) spatial positions of the array of transducer elements relative to the target and/or (ii) beam phase center positions of the array, in which the acoustic signal transmission couplant includes an acoustic coupling component including a hydrogel material operable to conduct the acoustic waveforms between the transducer elements and a receiving medium in contact with the acoustic coupling component, in which the acoustic coupling component is capable to conform to the receiving medium and the transducer element such that there is an acoustic impedance matching between the receiving medium and the transducer element, and in which the transmitted acoustic waveforms and the returned acoustic waveforms produce an enlarged effective aperture.

Example 28 includes the method of example 27, further including processing the received returned acoustic waveforms to produce an image of at least part of the target.

As noted earlier, some of the disclosed embodiments relate to an acoustic coupling medium including a hydrogel formed from one or more polymerizable materials and capable of conforming or molding into specific three dimensional shapes for use in tomographic ultrasound imaging, large aperture ultrasound imaging, and therapeutic ultrasound.

Hydrogel materials contain mostly water, thus, the acoustic wave speed of the hydrogel is dominated by water. The acoustic wave speed in water is approximately proportional to temperature through a high order empirically-determined polynomial relationship from 0 to 100° C. The acoustic wave speed of pure water varies from 1482 m/s to 1524 m/s from 20° C. to 37° C., respectively. Thus, the acoustic wave speed in a polymeric material will vary with temperature.

A material with a calibrated acoustic wave speed may be used in combination with a delay-and-sum beamformer to correct the propagation times on transmission and reception in order to reduce image distortion created by uncalibrated coupling materials. For example, the location of a structure such as a tissue-bone interface is ambiguous without knowledge of the average acoustic wave speed between the array and the bone. The true location of the bone may be deeper or shallower than it measures on the ultrasound image.

A material with a temperature calibrated acoustic wave speed such that the material may be heated in order to provide a more comfortable interface to the patient without creating image distortion. Besides patient comfort, a heated material also supports increased blood flow in the region in contact with the patient and in regions peripheral to the region in contact, thus facilitating more accurate Doppler measurements. A material with a calibrated acoustic wave speed will also function optimally at a target temperature (e.g. 37° C.) or target range of temperatures (e.g. 20-37° C.).

Thermocouples, thermistors, fiber-optic thermometers or other temperature sensing devices may be implanted into the hydrogel to provide real-time temperature feedback. Additionally, wires, resistors, thermopiles, electrical current, infrared radiation, water pipes, conduction, or other means to heat the hydrogel may be utilized to heat the gel. A temperature feedback and control device may be utilized to precisely and accurately control the temperature of the hydrogel.

The disclosed acoustic coupling medium can be employed in acoustic imaging, range-Doppler measurement, and therapeutic systems to transfer emitted and returned acoustic waveforms between such acoustic systems and a receiving medium, such as tissue of a living organism.

In some implementations of the disclosed acoustic coupling technology, for example, a hydrogel acoustic coupling medium of the present technology can provide spatially-varying acoustic absorption for use with acoustic imaging, diagnostic and/or therapeutic devices or systems to provide tomographic ultrasound imaging, large aperture ultrasound imaging arrays, and therapeutic ultrasound arrays for such acoustic devices and systems. In some implementations of the disclosed technology, the hydrogel acoustic coupling medium can couple acoustic waves from acoustic energy sources into the hydrogel acoustic coupling medium and subsequently into secondary media with acoustic sound speeds ranging from 1400 m/s up to 1700 m/s. Examples of the secondary media include, but are not limited to, mammalian tissues and water. The secondary media may contain structures with sound speeds outside the sound speed range of the coupling medium, e.g., such as bone, implanted devices, plastics, ceramics, glass, and metals.

In practical applications of ultrasound imaging, particularly for imaging human and nonhuman animals, ultrasound image formation typically occurs in the near field of an acoustic emission aperture, which poses several challenges for obtaining high resolution and quality ultrasound images. For example, in such ultrasound imaging applications, generally, one or more transducer elements are included in an acoustic imaging device, forming an array, to generate the acoustic aperture. These transducer elements typically require several wavelengths to transition from the near field to the far field regime following an acoustic emission, thus requiring an acoustic buffer region, also known as an acoustic standoff. For example, this acoustic buffer region or acoustic standoff may be necessary for image formation close to the acoustic aperture. Furthermore, focused image formation typically requires that the ratio of the focal depth divided by the aperture size (e.g., also known as the f-number) be greater than one, e.g., for points of the image formation closest to the acoustic aperture. Likewise, the acoustic standoff is necessary for image formation close to the acoustic aperture in order to satisfy the f-number condition.

In implementations of the disclosed technology, the image formation is generated using combinations of the transducer elements, in which a selected group of transducer elements are used to produce an acoustic emission followed by reception of return acoustic echoes on some, the same, and/or other transducer elements of the group. For example, the transducer elements producing the acoustic emission are referred to as transmit elements. Likewise, the transducer elements that receive the return acoustic echoes are referred to as receive elements. In some examples, the combinations may be divided into combinations of individual pairs of transmit and receive elements such that the linear combination of the pairs produces an approximately equivalent image as obtained using the combinations of one or more elements on both transmit and receive. For example, each time sample of an echo recorded from the pair of transmit and receive elements is an integration of acoustic reflectivity over the corresponding round-trip time or time delay corresponding to the time sample. The integration is a line integral over linear paths of the constant round-trip time or time delay. The linear paths can be circular or elliptical as determined by the location of the pair of transmit and receive elements. In practice, for example, the circular or elliptical paths may extend to highly reflective interfaces including, but not limited to, the interface between the acoustic coupling medium and a low acoustic impedance material, e.g., such as air or plastic, or the interface between the acoustic coupling medium and a high acoustic impedance material, e.g., such as metal or ceramic.

Acoustic reflections from the interfaces, also known as specular reflections, contaminate the line integrals of reflectivity and the corresponding echo samples obtained from the transmit and receive combinations. In general, for the acoustic reflections observed for the combination of transmit and receive elements, the angle of incidence measured from the transmit element to a point on the reflective interface to the surface normal vector for a point lying on the reflective interface equals the angle of reflection measured from the same normal vector to the vector defined by the point on reflective interface to the receive element. The acoustic reflection can have mirror or amphichiral symmetry. The acoustic reflection has power equal to the acoustic impedance of the secondary medium minus the acoustic impedance of the coupling medium, divided by the acoustic impedance of the secondary medium plus the acoustic impedance of the coupling medium, as described in Equation (1).

$$P_r = \frac{(Z_{2m} - Z_{cm})}{(Z_{2m} + Z_{cm})} \quad (1)$$

The contamination caused by the acoustic reflection can preclude the use of the transmit and receive combinations in beamformers based on delayed and summed echo samples, also known as a delay-and-sum beamformer. Such preclusion of echo samples can result in removal of the transmit and receive combination from the delay-and-sum beamformer, thus limiting the quality of the image pixel corresponding to the delay-and-sum beamformer. The image pixel quality is a function of the point-spread-function of the limited set of transmit and receive combinations. Such preclusion of echo samples can also reduce the signal-to-noise ratio (SNR) for the image pixel. Additionally, for the apertures with an array pitch greater than one-half wavelength, the image pixel locations that require transmitter and receiver combinations to steer away from zero degrees (0°) will be increasingly subject to grating lobes with increasing steering angle and increasing array pitch. Such grating lobes add to the sensitivity and complexity of the specular reflections.

The acoustic coupling medium of the disclosed technology can be configured in an acoustic couplant device and operable to conduct acoustic signals between a transducer element disposed in a housing body of the couplant device and a receiving medium (i.e., the secondary medium, e.g., skin of a subject) in contact with the acoustic coupling medium to propagate the acoustic signal toward a target volume. The disclosed acoustic coupling medium is capable to conform to the target volume such that there is an acoustic impedance matching (e.g., very low reflection) between the receiving medium and the transducer element.

Figure 5A:
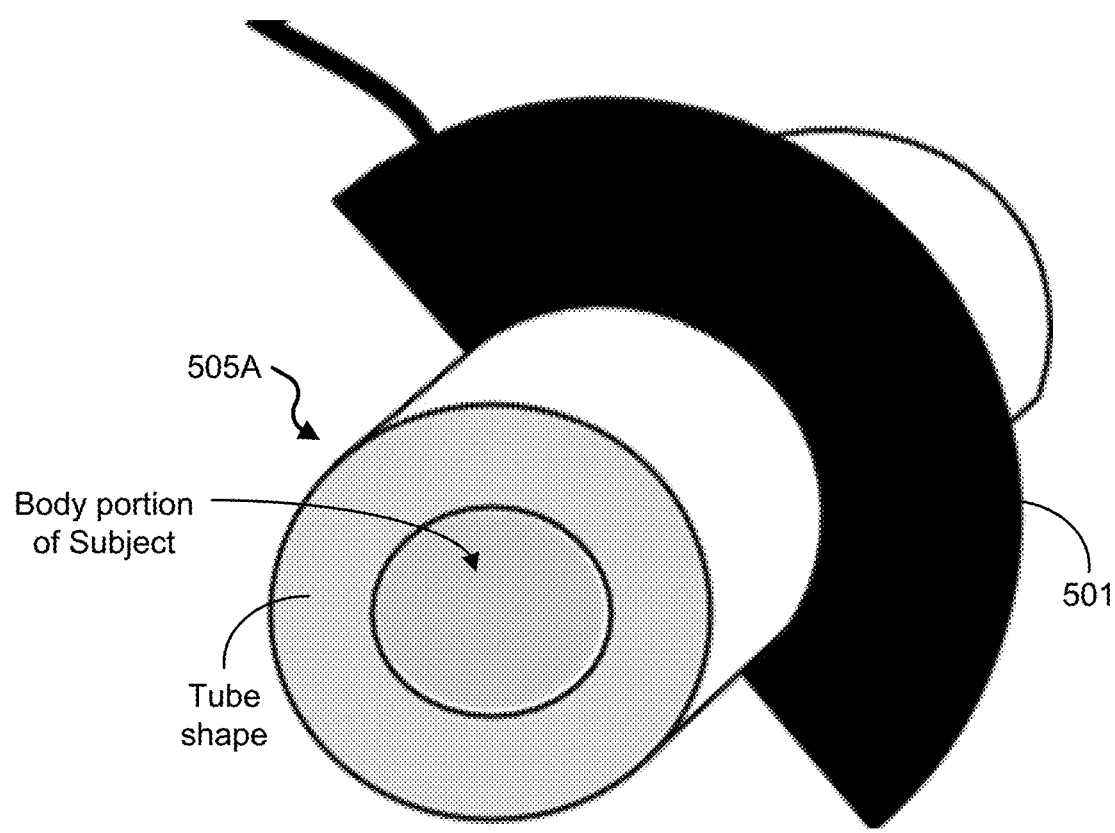
FIG. 5A shows an exemplary embodiment of an acoustic coupling medium.

The disclosed acoustic coupling medium is configured to have three-dimensional shape. In some examples of the disclosed acoustic coupling medium, for example, an acoustic coupling medium is engineered into a specific three-dimensional shape for a particular implementation utility, e.g., for tomographic acoustic imaging, large aperture acoustic imaging, and/or therapeutic acoustic treatment. In one example embodiment shown in FIG. 5A, an acoustic coupling medium 505A includes shape of a tube with an inner radius, an outer radius, and a height. The tubular acoustic coupling medium 505A includes a hydrogel including one or more polymerizable materials and capable of conforming or molding into specific three dimensional shapes for desired applications. The radii and the height of the acoustic coupling medium 505A can vary based on each application. For example, due to the elasticity and tensile strength of the coupling medium 505A, the tubular shape is flexible and capable of stretching around irregularly shaped secondary media, e.g., such as limbs of a human or nonhuman animal. As shown in FIG. 5A, the acoustic coupling medium 505A is attached to the housing body 501 of an acoustic couplant device. The acoustic coupling medium 505A is configured such that, when placed in contact with a subject, the coupling medium 505A also maintains constant contact with the secondary media of the subject, e.g., maintaining complete contact with the subject's skin, including around irregular structures such as elbows and knees.

Additionally, the tubular coupling medium is compatible with tomographic apertures ranging from 0 to 360 degrees around the secondary medium, e.g., subject's limbs, torso, head, etc., while maintaining acoustic contact over the entire aperture and secondary medium, simultaneously. With applied force, constant contact may be maintained with movement of the aperture over the coupling medium. For example, the tomographic apertures with a polygon shape, the flexible coupling medium maintains contact over the surface of the entire aperture, including between facets of the polygon. The exemplary tubular shape of the acoustic coupling medium 505A may be molded to match any three-dimensional shape of the aperture, including polygon shapes. For example, for tomographic apertures less than 360 degrees, the exemplary tubular acoustic coupling medium 505A does not have highly reflective air interfaces at sharp edges that would exist for coupling media extending only over the aperture. At the edges of the aperture, the transmit and receive combinations are able to function unrestricted by the tubular coupling medium 505A, thus obviating the need for preclusion of the combination from the beamformer. The reflective air interface extending around the entire coupling medium keeps wide angle and primary reflections internally reflecting around the acoustic coupling medium 505A, where they are attenuated and end up being incoherent acoustic noise.

Figure 5B:
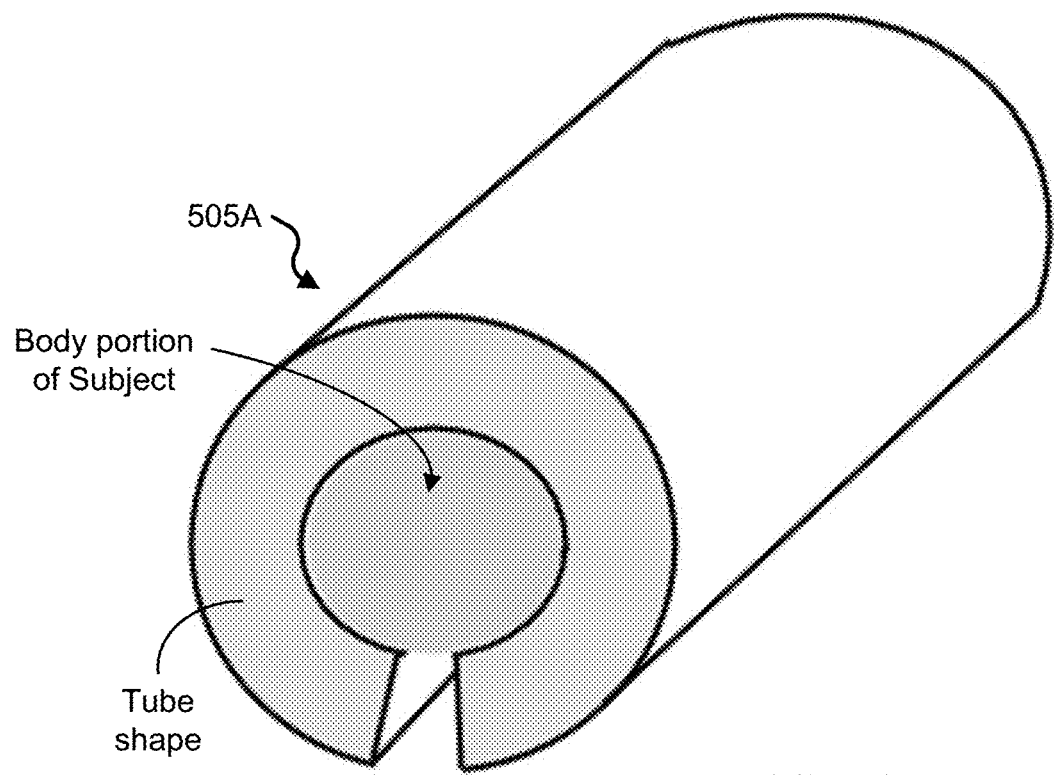
FIG. 5B shows another exemplary embodiment of an acoustic coupling medium.

FIG. 5B shows another arrangement of the exemplary tubular acoustic coupling medium 505A placed in contact with a body portion of the subject to conform with complete contact with the secondary medium. The example arrangement shown in FIG. 5B provides the ability for the internal reflections to be further broken up by one or more gaps in the tubular acoustic coupling medium 505A.

Figure 5C:
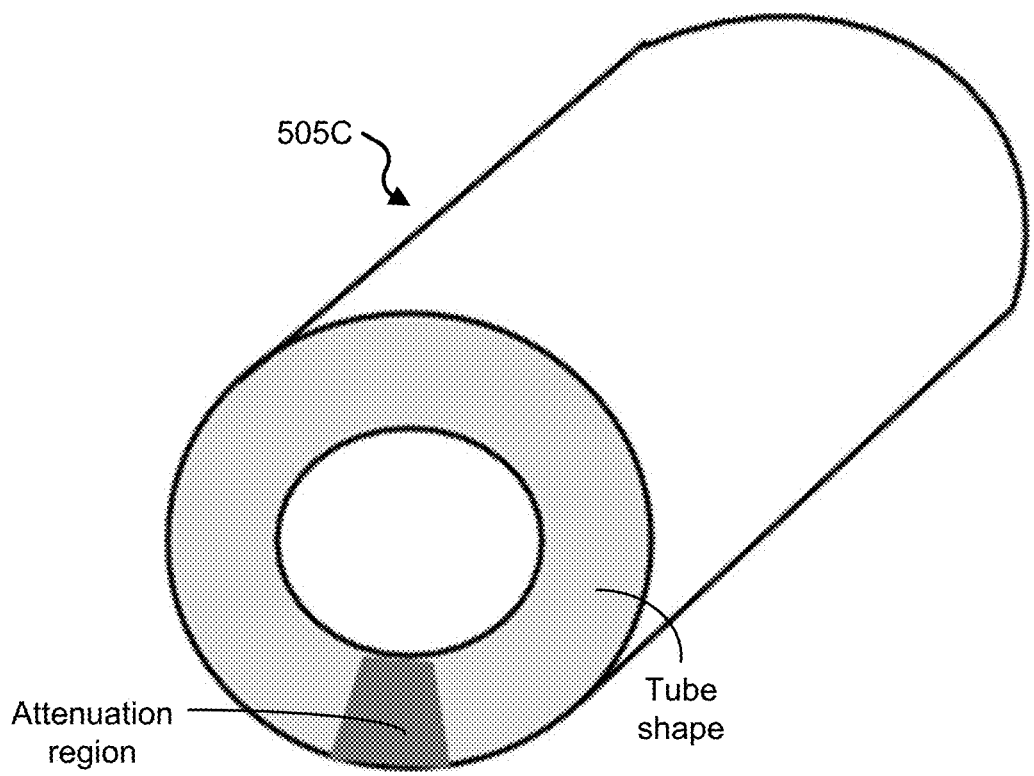
FIG. 5C shows another exemplary embodiment of an acoustic coupling medium.

FIG. 5C shows another example embodiment of an acoustic coupling medium 505C that includes the hydrogel and an acoustically attenuating region in one or more portions of the hydrogel. For example, in acoustic transmission operations, the internal reflections may be absorbed with the acoustically attenuating region in the tubular acoustic coupling medium 505C. For example, such attenuation may be obtained through absorption or scattering or both. The acoustic attenuation region can be structured to include one or more of higher density polymers, higher absorption polymers, scatterers, microbubbles, microballoons, plastics, rubbers, or other absorptive materials.

Figure 5D:
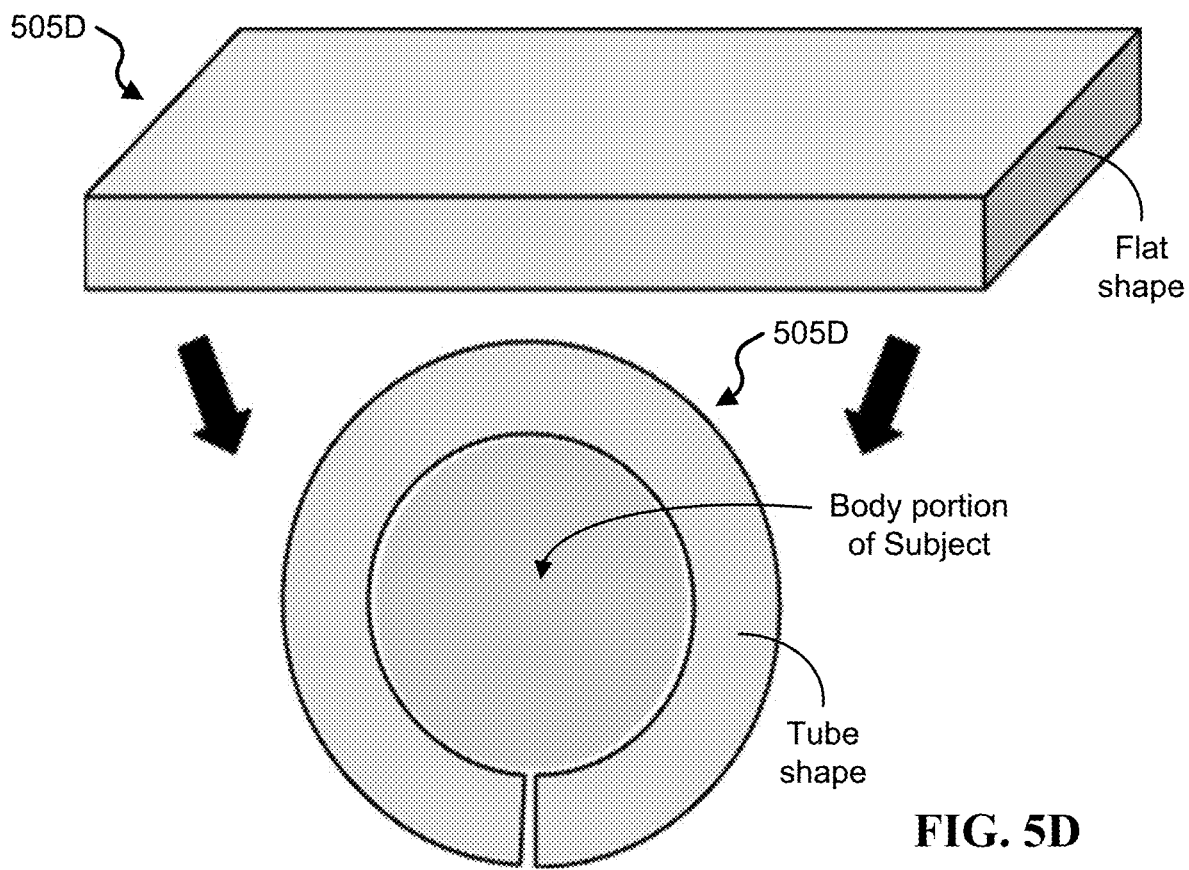
FIG. 5D shows another exemplary embodiment of an acoustic coupling medium.
Figure 5E:
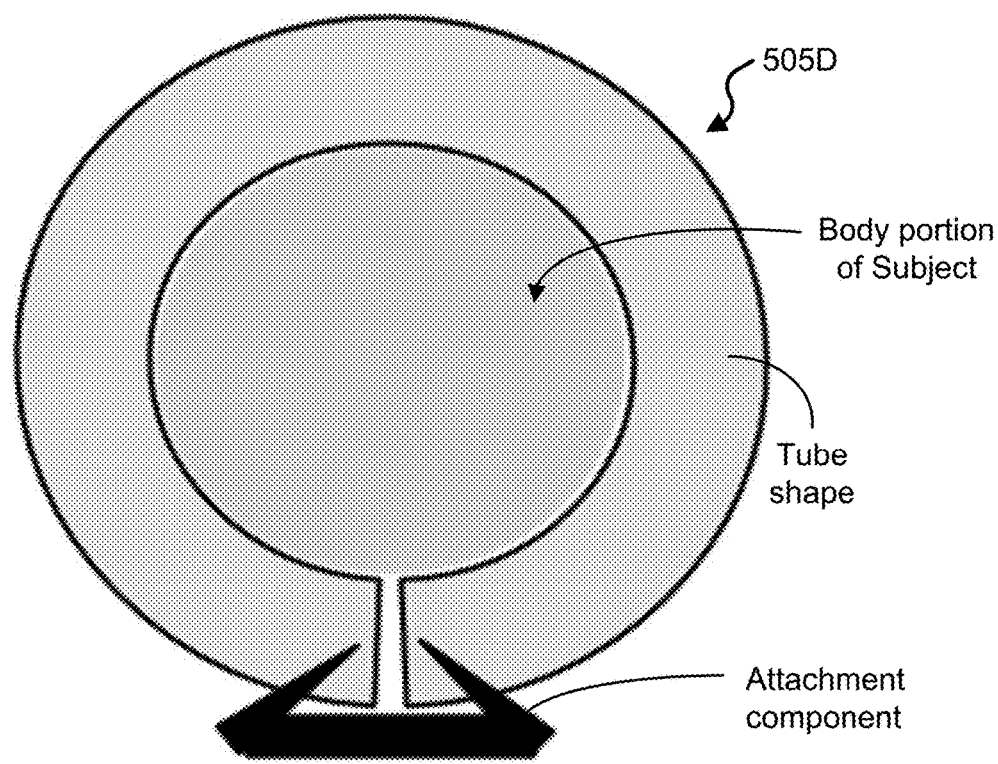
FIG. 5E shows another exemplary embodiment of an acoustic coupling medium.

FIG. 5D shows another example embodiment of an acoustic coupling medium 505D that includes the hydrogel and configured in a flattened shape convertibly adapted to a tubular shape. For example, the tubular shape may be formed from a rectangular block of the acoustic coupling medium 505D, which is wrapped around the secondary medium (e.g., of the subject). The wrapped coupling medium may be trimmed using a cutting device and attached end-to-end with an attachment device, e.g., including, but not limited to, straps, velcro, buttons, zipper, latch, gripper, or some other mechanical attachment device, or a chemical bond. FIG. 5E shows an example of the shape convertible acoustic coupling medium 505D conformed around a body portion of a subject and attached at contactable ends by an attachment component.

Figure 5F:
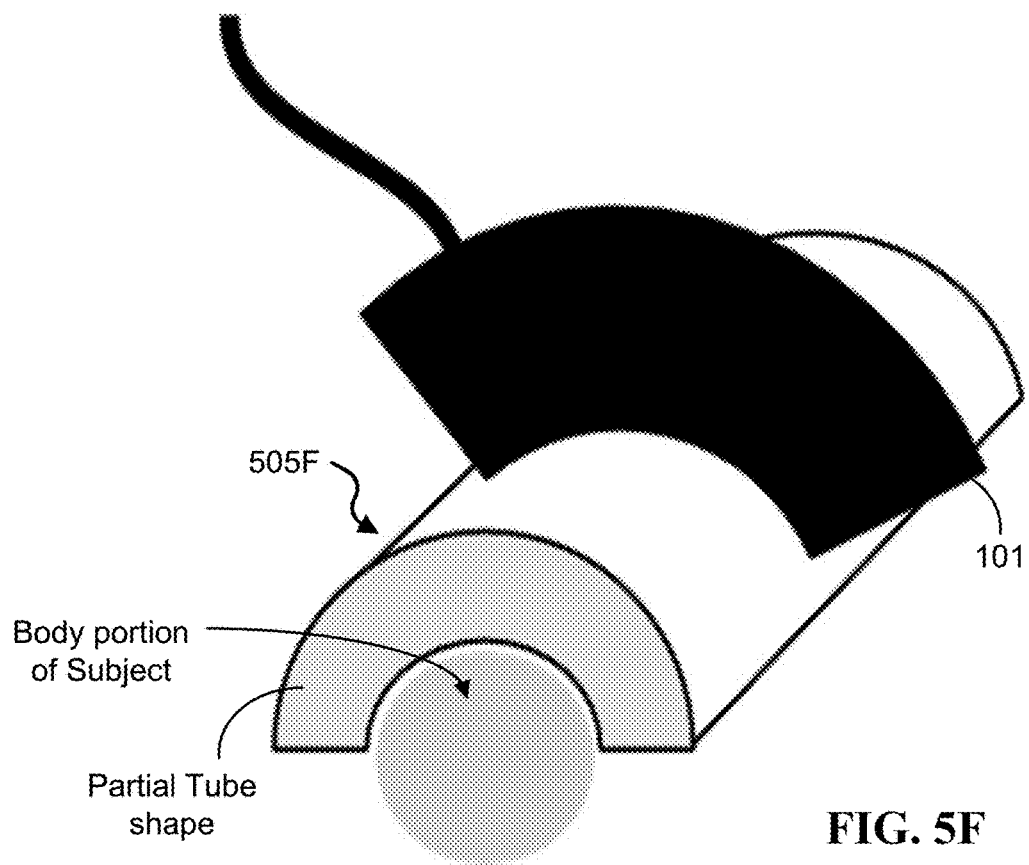
FIG. 5F shows another exemplary embodiment of an acoustic coupling medium.

In addition to a tubular shape, the acoustic coupling medium may be shaped with a partial tubular shape of less than 360 degrees in the transverse plane, such that it can partially cover the secondary medium of the subject, e.g., subject's limbs, torso, head, etc., and can extend up to or beyond the boundaries of the aperture, as shown in FIG. 5F. FIG. 5F shows another example embodiment of an acoustic coupling medium 505F that includes the hydrogel and configured in a partial tubular shape that is less than 360 degrees conformed to a subject's body portion. The acoustic coupling medium is shown in FIG. 5F to be attached to the body housing 101 of an acoustic couplant device.

Figure 5G:
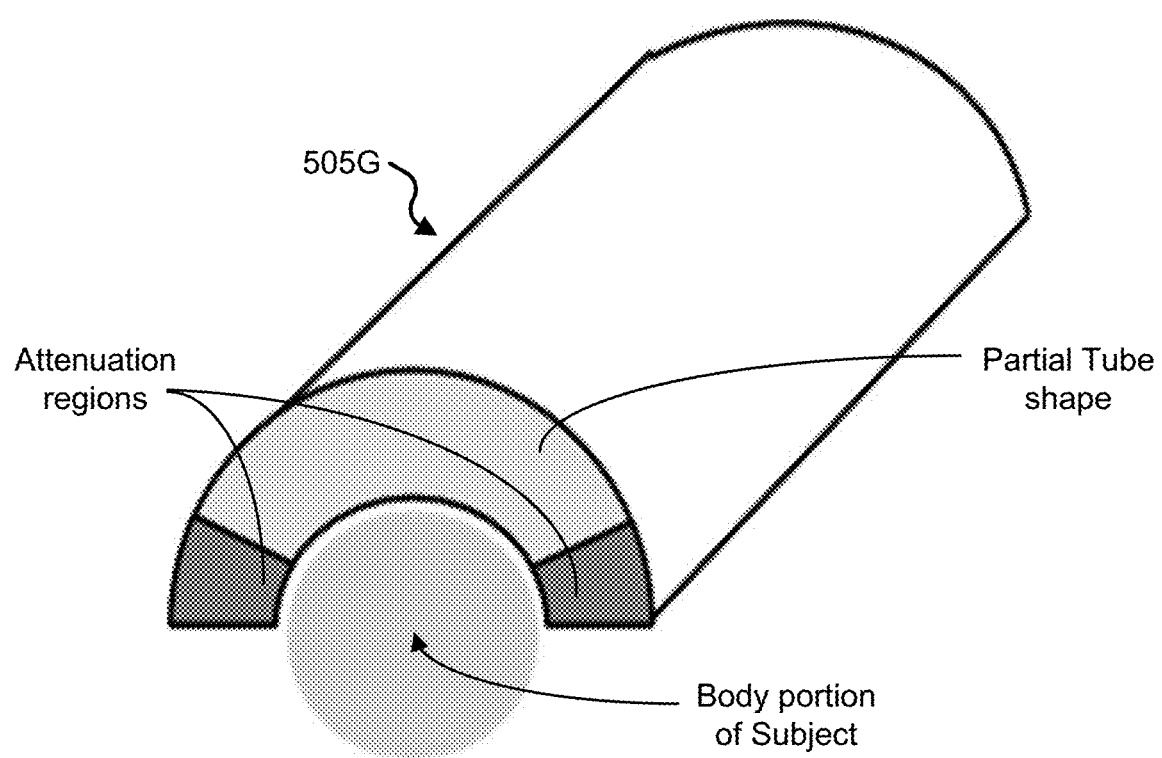
FIG. 5G shows another exemplary embodiment of an acoustic coupling medium.

In some embodiments of the acoustic coupling medium, the partial tubular acoustic coupling medium 505F may be structured to include acoustically attenuating regions in one or more portions of the acoustic coupling medium. As shown in FIG. 5G, an acoustic coupling medium 505G includes the hydrogel and two acoustic attenuating regions located at ends of the partial tube coupling shape to provide acoustically attenuating properties to the acoustic coupling medium 505G.

In various embodiments of the disclosed acoustic coupling medium, the hydrogel can include one or more polymerizable materials that polymerize in the presence of water into hydrophilic gels formed from a natural or synthetic network of polymer chains. Examples of such polymerizable materials include, but are not limited to, polymers and polymer derivatives, alginate, agarose, sodium alginate, chitosan, starch, hydroxyethyl starch, dextran, glucan, gelatin, Poly(vinyl alcohol) (PVA), Poly (N-isopropylacrylamide) (NIPAAm), Poly(vinylpyrrolidone) (PVP), Poly(ethylene glycol) (PEG), Poly(acrylic acid) (PAA), acrylate polymers, Polyacrylamide (PAM), Poly(hydroxyethyl acrylate) (PHEA), Poly(2-propenamide), Poly(1-carbamoylethylene), and Poly(hydroxyethyl methacrylate) (PHEMA). In fabrication techniques to produce the hydrogel, the polymerizable materials can be polymerized through several processes, which may involve toxic or non-toxic chemical compounds, ultraviolet light, irradiation, toxic or nontoxic solvents, temperature cycling, and freeze-thaw cycling. In some implementations to produce the hydrogel, polymerization of the hydrogel through freeze-thaw cycling can be performed, due to the absence of potentially toxic compounds.

For example, the hydrogel can include a material structure that allows acoustic signal propagation with an attenuation factor of 1.0 dB/MHz/cm or less, an impedance of 2.0 MRayls or less, and a longitudinal speed of sound of 1700 m/s or less at 20° C. The acoustic coupler 105 is engineered to have a % elongation of 100% or greater, a density ranging from 1.00-1.20 g/cm$^3$, a shear modulus of less than 1 MPa, and melting and freezing points near 70° C. and −5° C., respectively. For example, the hydrogel material can be at least 90% water and have a pH of ~7.0.

In a some embodiments of the acoustic coupling medium, the hydrogel can primarily include water or equivalent solvent and the polymer Poly(vinyl alcohol) (PVA) through the example polymerization process of freeze-thaw cycling, which is a biocompatible polymer and a biocompatible polymerization process for the polymer. The addition of other components, e.g., such as solvents (such as ethyl alcohol or dimethyl sulfoxide) and/or other polymers (such as alginate or gelatin), to this example PVA hydrogel may be employed, as such additional components can be used to improve mechanical or acoustic properties. For example, the addition of one or more bacteriostatic chemicals with sufficient concentration and compatibility with the hydrogel integrity can maintain sterility of the hydrogel during storage and use. Notwithstanding other mechanically, acoustically, and biologically equivalent formulations, the utility of a hydrogel for its acoustic properties due to its high water content, its high tensile strength, and its elasticity is an advantageous feature of the disclosed acoustic coupling medium. The sound speed and acoustic attenuation of the hydrogel may be controlled by varying polymer concentration, water concentration, additional solvent concentration, degree of polymerization, method of polymerization, and inclusion of additional materials such as scattering and/or acoustically absorbing materials.

In one embodiment, for example, the hydrogel includes PVA in a weight ratio of 1-10% and $H_2O$ in a weight ratio of 90-99%. The hydrogel is cross-linked through application of 1-10 controlled freeze-thaw cycles cycling in the range of −40° C. to 70° C.

In another embodiment, for example, the hydrogel includes PVA in a weight ratio of 1-10%, DMSO in a weight ratio of 1-10%, and $H_2O$ in a weight ratio of 80-98%. The hydrogel is cross-linked through application of 1-10 controlled freeze-thaw cycles cycling in the range of −40° C. to 70° C.

In another embodiment, for example, the hydrogel includes PVA in a weight ratio of 4-10%, PVP in a weight ratio of 1-5%, DMSO in a weight ratio of 1-10%, and $H_2O$ in a weight ratio of 75-94%. The hydrogel is cross-linked through application of 1-10 controlled freeze-thaw cycles cycling in the range of −40° C. to 70° C.

In another embodiment, for example, the hydrogel includes PVA in a weight ratio of 4-10%, PVP in a weight ratio of 1-5%, polyethylene glycol in a weight ratio of 1-5%, and $H_2O$ in a weight ratio of 80-94%. The hydrogel is cross-linked through application of 1-10 controlled freeze-thaw cycles cycling in the range of −40° C. to 70° C.

In another embodiment, for example, the hydrogel includes PVA in a weight ratio of 4-10%, PVP in a weight ratio of 1-5%, sodium tetraborate in a weight ratio of 1-5%, and $H_2O$ in a weight ratio of 80-94%. The borate ions react with hydroxyl groups to cross-link the polymer. The mixture is maintained at a constant temperature during cross-linking.

Figure 6:
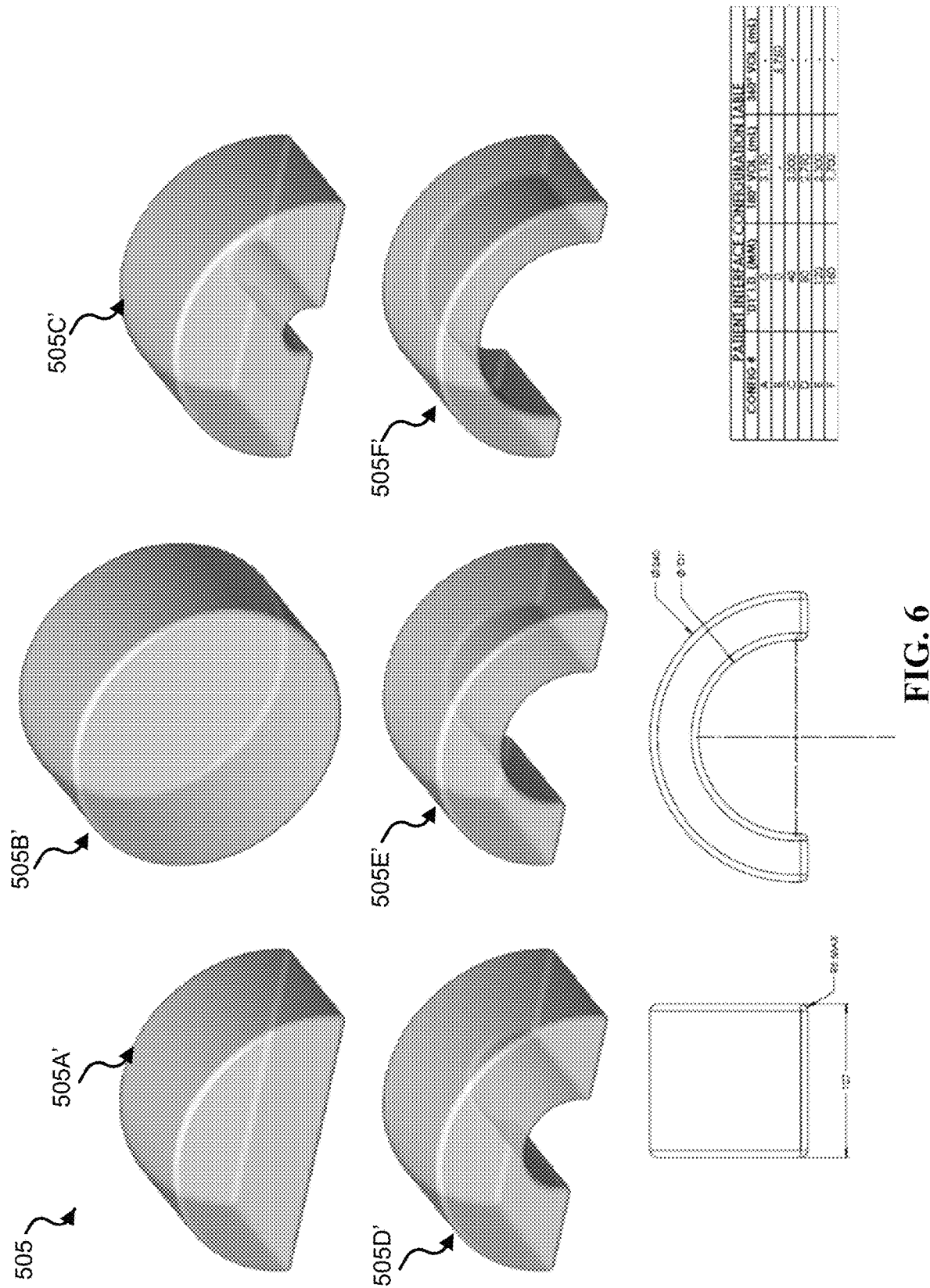
FIG. 6 shows schematic diagrams of an exemplary acoustic coupling medium formed in various shapes, sizes, and configurations.

FIG. 6 shows three dimensional schematic diagrams of an exemplary acoustic coupling medium 505 formed in various shapes, sizes, and configurations. In one example, an acoustic coupling medium 505A' is configured to have a shape similar to a half cylinder with a 180° curvature, and diameter and depth designed to an initial size, and which are variable to conform to a particular receiving body. In this example, the acoustic coupling medium 505A' can be configured to have a volume of 3.15 L, which is retained in any shape to which the acoustic coupling medium 505A' is conformed. In another example, an acoustic coupling medium 105B' is configured to have a cylindrical shape with a diameter and depth designed to an initial size, and which are variable to conform to a particular receiving body. In this example, the acoustic coupling medium 105B' can be configured to have a volume of 5.75 L. In other examples, acoustic coupling mediums 505C', 505D', 105E', and 505F' are configured to have a half-cylinder shape similar to a half donut with a 180° curvature and initial outer diameter and depth designed to an initial size, in which the initial inner diameter of the acoustic coupling mediums 505C', 505D', 105E', and 505F' is designed to differing sizes (e.g., 40, 80, 120, and 160 mm, respectively), and which the sizes are variable to conform to a particular receiving body, e.g., such as surround the subject's arm, leg, neck, etc. In these examples, the acoustic coupling mediums 505C', 505D', 105E', and 505F' can be configured to have a volume of 3.0 L, 2.75 L, 2.3 L, and 1.7 L, respectively.

Figure 7A:
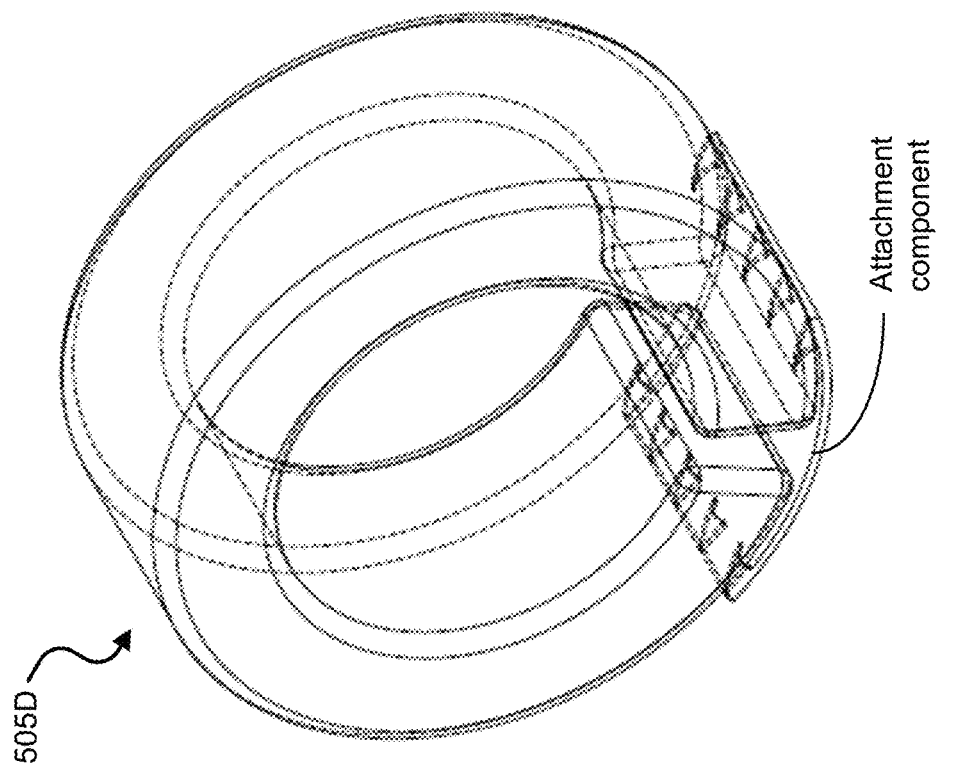
FIG. 7A shows schematic diagram of an exemplary embodiment of the acoustic coupling medium with an attachment component.
Figure 7A:
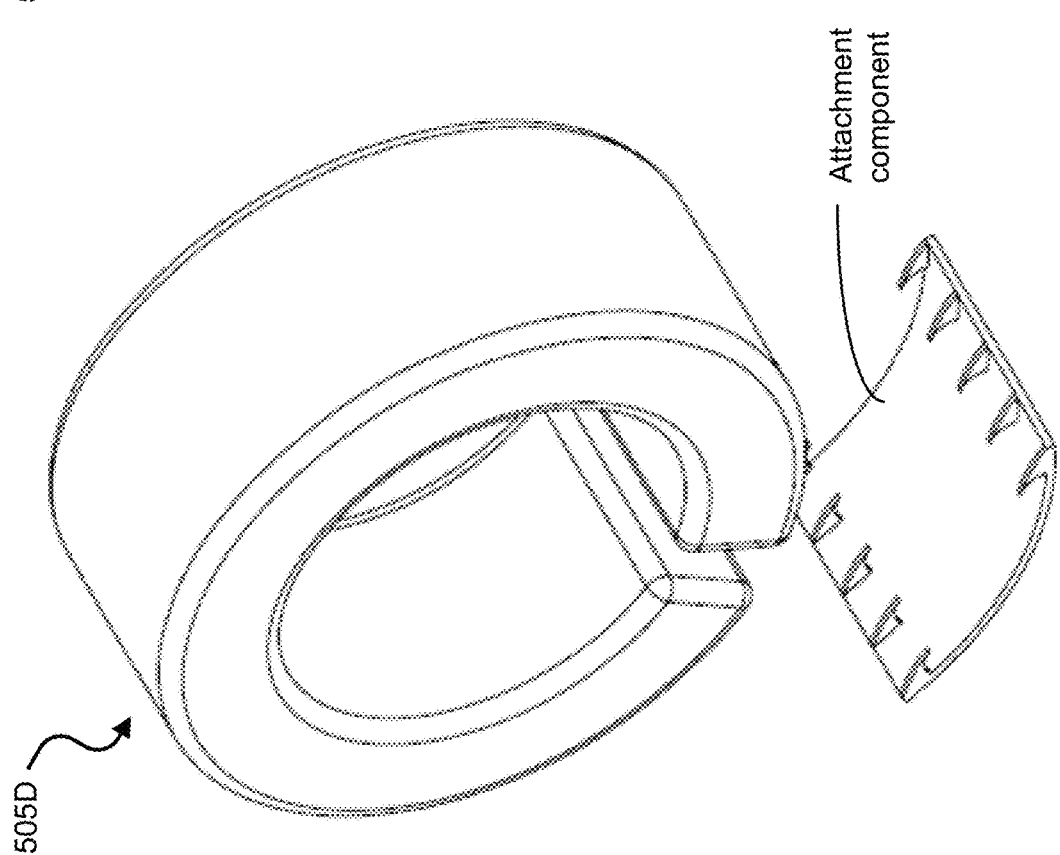
Figure 7B:
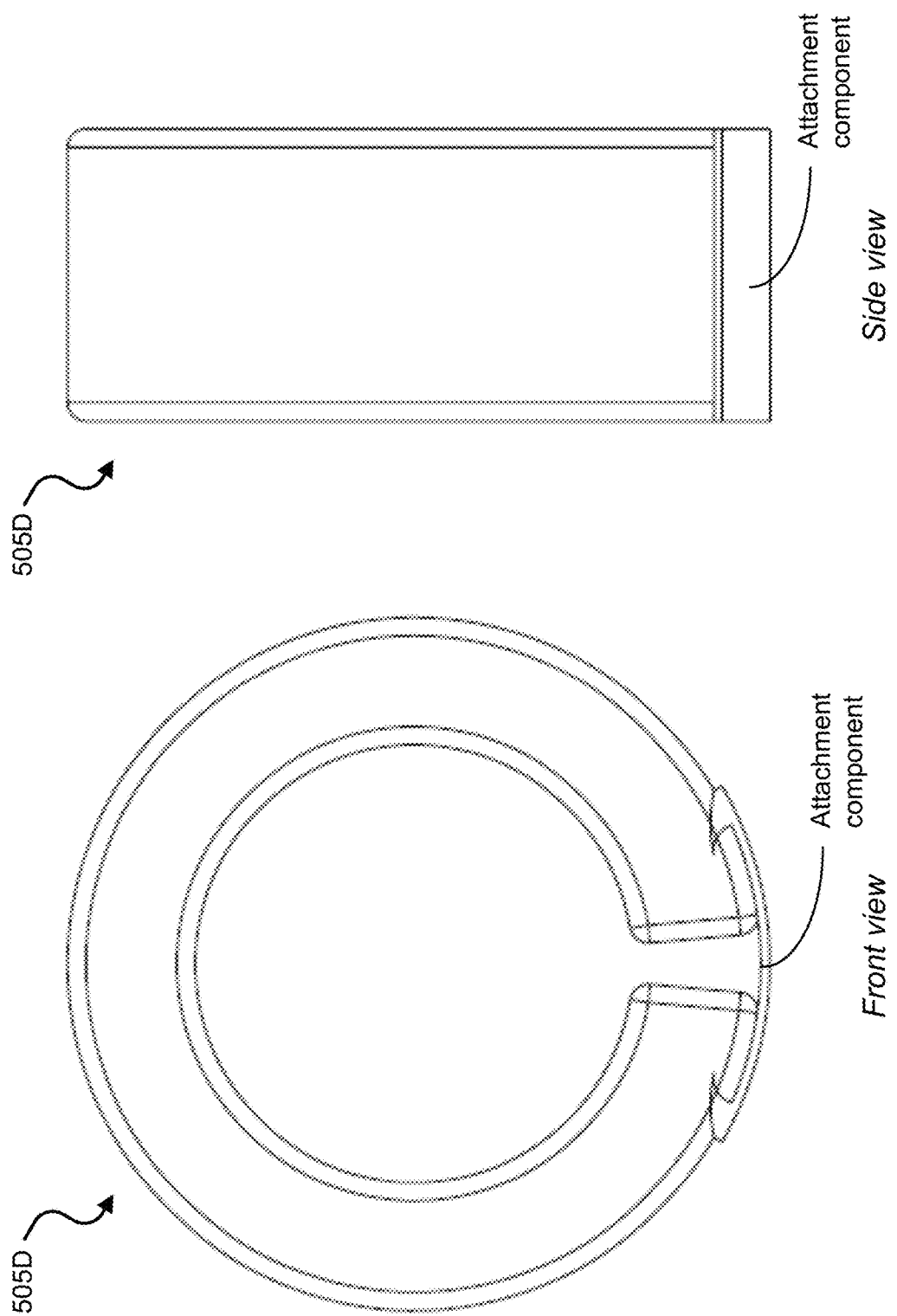
FIG. 7B shows front and side schematic views of an exemplary embodiment of the acoustic coupling medium with an attachment component.
Figure 7C:
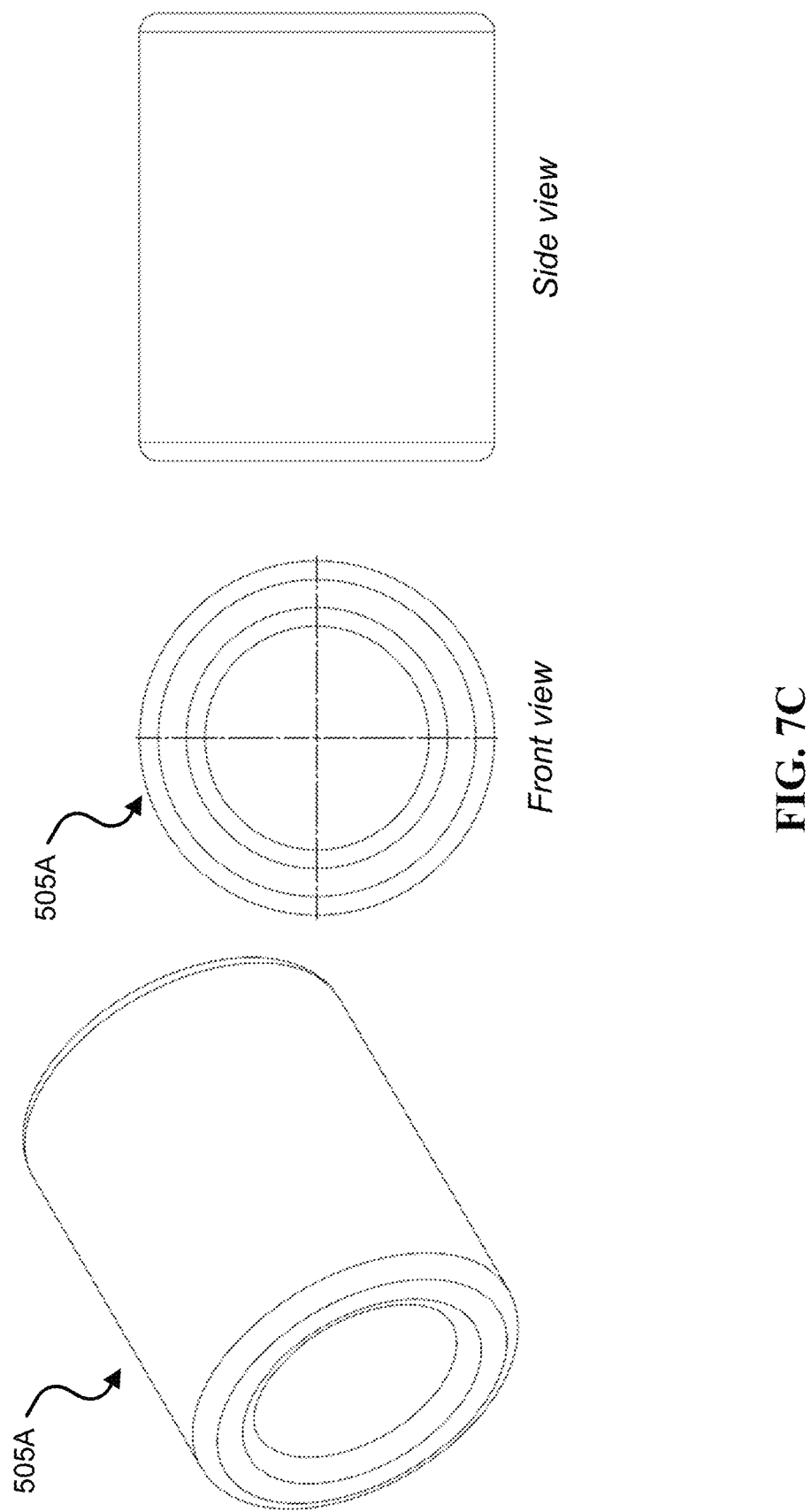
FIG. 7C shows different schematic views of an exemplary embodiment of the acoustic coupling medium with a tubular curved shape.

FIGS. 7A-7C show schematic diagrams of exemplary embodiments of the acoustic coupling medium 505D and 505A, featuring three dimensional, front, and side views. As shown in FIG. 7A, the acoustic coupling medium 505D includes the hydrogel configured in a tubular curved shape, which may be wrapped around the secondary medium of the subject and secured by attachment of the attachment component on each end of the hydrogel. The left drawing of FIG. 7A shows a three dimensional schematic view of the hydrogel and the attachment component of the acoustic coupling medium 505D presently detached, and the right drawing of FIG. 7A shows a transparent three dimensional schematic view of the hydrogel secured in the tubular configuration by attachment of the attachment component. In the examples shown in FIG. 7A, the attachment component is structured to include a curved base portion that is sized to the initial size of the depth of the hydrogel and having the same arc curvature as the hydrogel in the tubular configuration. The attachment component is structured to include one or more sets of opposing protrusion structures on the inside surface of the base portion capable of penetrating into the hydrogel to secure the hydrogel in the tubular shape. FIG. 7B shows a transparent front view and a transparent side view of the acoustic coupling medium 505D with the attachment component secured to the hydrogel.

FIG. 7C shows the acoustic coupling medium 505A including the hydrogel configured in a 360° tubular curved shape. The left drawing shows a three dimensional schematic view of the acoustic coupling medium 505A, the center drawing shows a front view of the acoustic coupling medium 505A, and the right drawing shows a side view of the acoustic coupling medium 505A. As depicted in the drawings of FIG. 7C, in this example, the acoustic coupling medium 505A includes a beveled edge at the interface between the outer circular plane surfaces and the outer curved surface, as well as a beveled edge between the outer circular plane surfaces and the inner curved surface. For example, the beveled edge may provide easier and secure loading and unloading of the coupling medium 505A in and out of a bracket or other holder of an acoustic couplant device.

Figure 8:
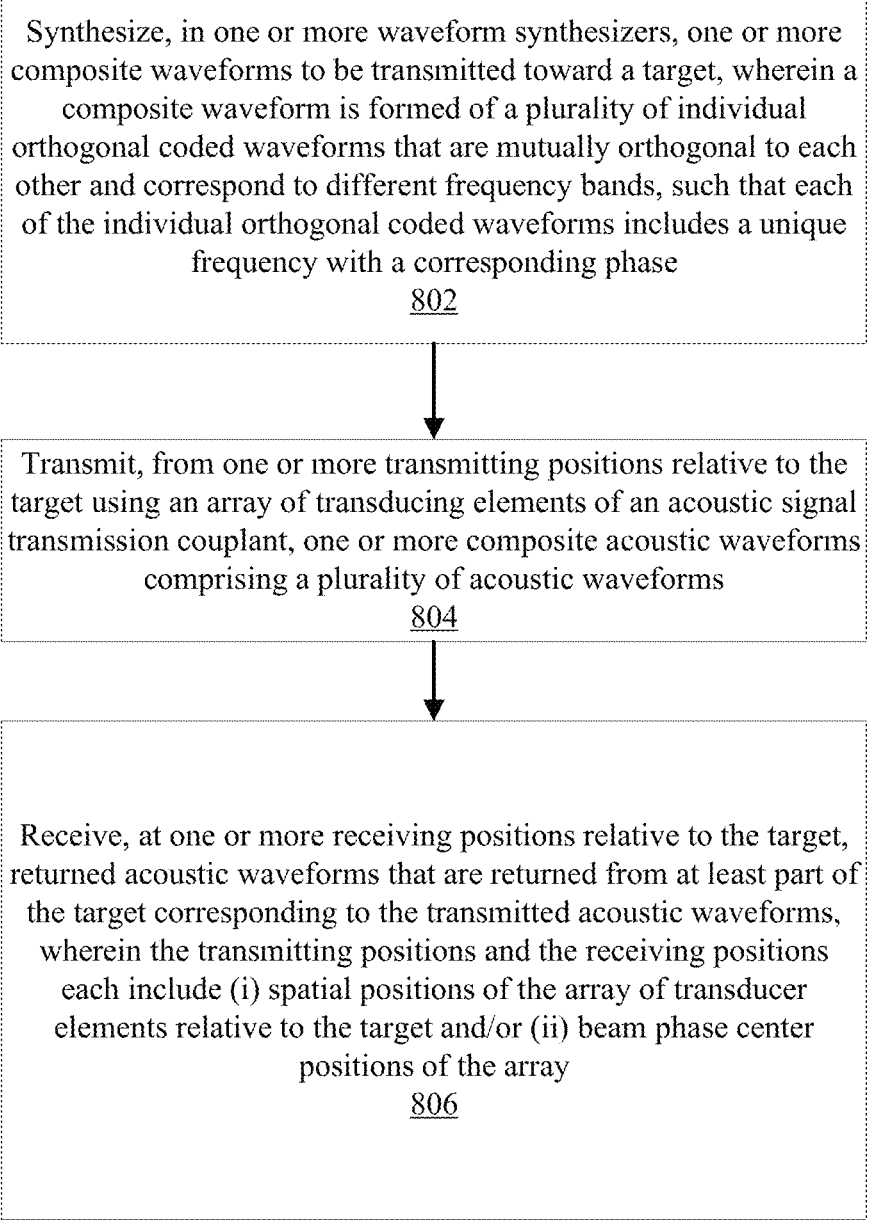
FIG. 8 illustrates a set of operations that can be carried out to produce acoustic waveforms using an acoustic impedance matched couplant in accordance with an exemplary embodiment.

FIG. 8 illustrates a set of operations that can be carried out to produce acoustic waveforms using an acoustic impedance matched couplant in accordance with an exemplary embodiment. At 802, in one or more waveform synthesizers, one or more composite waveforms are synthesized to be transmitted toward a target. A composite waveform is formed of a plurality of individual orthogonal coded waveforms that are mutually orthogonal to each other and correspond to different frequency bands such that each of the individual orthogonal coded waveforms includes a unique frequency with a corresponding phase. At 804, one or more composite acoustic waveforms are transmitted, from one or more transmitting positions relative to the target using an array of transducing elements of an acoustic signal transmission couplant. The one or more composite acoustic waveforms include a plurality of acoustic waveforms, and the transmitting includes selecting one or more of the transducing elements of the array to transduce the plurality of individual orthogonal coded waveforms of the respective one or more composite waveforms into the plurality of corresponding acoustic waveforms of the respective one or more composite acoustic waveforms. At 806, at one or more receiving positions relative to the target, returned acoustic waveforms are received that are returned from at least part of the target corresponding to the transmitted acoustic waveforms. Reception of the returned acoustic waveforms includes selecting at least some of the transducing elements of the array to receive the returned acoustic waveforms. When conducting the above operations, the transmitting positions and the receiving positions each include (i) spatial positions of the array of transducer elements relative to the target and/or (ii) beam phase center positions of the array. Further, the acoustic signal transmission couplant includes an acoustic coupling component including a hydrogel material operable to conduct the acoustic waveforms between the transducer elements and a receiving medium in contact with the acoustic coupling component. The acoustic coupling component is capable of conforming to the receiving medium and the transducer element such that there is an acoustic impedance matching between the receiving medium and the transducer element. The transmitted acoustic waveforms and the returned acoustic waveforms produce an enlarged effective aperture.

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

While this patent document contain many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. An acoustic coupling article for acoustic signal transmission, comprising:
   a semi-rigid material including a flexible, continuous pad and able to conform to both a surface of a receiving body and to an array of acoustic signal transducer elements, such that the semi-rigid material is operable to propagate acoustic signals between the acoustic signal transducer elements and a receiving medium of the receiving body and provide an acoustic impedance matching of 2.0 MRayls or less between the receiving medium and the acoustic signal transducer elements,
   wherein the acoustic coupling article is operable to propagate the acoustic signals with an attenuation factor of 1.0 dB/MHz-cm or less,
   wherein the acoustic coupling article includes at least one bracket component to secure and conform the semi-rigid material to the array of acoustic signal transducer elements, wherein the at least one bracket component and the semi-rigid material are coupled by one or more of:
   the at least one bracket component is at least partially embedded within the semi-rigid material;
   the at least one bracket component includes two or more clips, notches, or a combination thereof to enable attachment of the semi-rigid material to the at least one bracket component; or
   the semi-rigid material includes an adhesive region of the flexible, continuous pad to promote adhesion to the at least one bracket component;
   wherein the at least one bracket component includes an arch component to secure the semi-rigid material to interface each acoustic signal transducer element of the transducer elements of the array.

2. The acoustic coupling article of claim 1, wherein the acoustic coupling article includes at least one of: a shear modulus of 1 MPa or a density ranging from 1.00-1.20 $g/cm^3$.

3. The acoustic coupling article of claim 1, wherein the acoustic coupling article is operable to propagate the acoustic signals with a longitudinal speed of sound at 1700 m/s or less at 20° C., or capable to undergo a percent elongation of 100% or greater, or both.

4. The acoustic coupling article of claim 1, wherein the semi-rigid material includes one or more polymerizable materials that form a network structured to entrap an aqueous fluid inside.

5. The acoustic coupling article of claim 4, wherein the one or more polymerizable materials include one or more of alginate, agarose, sodium alginate, chitosan, starch, hydroxyethyl starch, dextran, glucan, gelatin, Poly(vinyl alcohol) (PVA), Poly (N-isopropylacrylamide) (NIPAAm), Poly(vinylpyrrolidone) (PVP), Poly(ethylene glycol) (PEG), Poly(acrylic acid) (PAA), acrylate polymers, Polyacrylamide (PAM), Poly(hydroxyethyl acrylate) (PHEA), Poly(2-propenamide), Poly(1-carbamoylethylene), or Poly(hydroxyethyl methacrylate) (PHEMA).

6. The acoustic coupling article of claim 4, wherein the aqueous fluid includes water, and wherein the water is at least 90% weight of the semi-rigid material.

7. The acoustic coupling article of claim 4, wherein the semi-rigid material is able to conform to the surface of the receiving body in complete contact to the surface without pockets of air or voids formed between the acoustic coupling article and the receiving body.

8. The acoustic coupling article medium of claim 4, wherein the semi-rigid material includes an acoustic attenuation region to scatter or absorb the acoustic signals in the attenuation region, the acoustic attenuation region including one or more of higher density polymers than the one or more polymerizable materials that form the network, a scattering material, microbubbles, microballoons, a plastic material, a rubber material, or an absorptive material.

9. The acoustic coupling article of claim 8, wherein the scattering material includes metal particles sized smaller than a wavelength of the acoustic signals or non-metal particles sized smaller than a wavelength of the acoustic signals, or wherein the scattering material includes graphite, silicon carbide, aluminum oxide, silicon oxide, or silver oxide.

10. The acoustic coupling article of claim 8, wherein the absorptive material includes silicone, polyurethane, or a polymer.

11. The acoustic coupling article of claim 1, further comprising an outer lining at least partially enclosing the semi-rigid material.

12. The acoustic coupling article of claim 1,
wherein the semi-rigid material is structured to have a tubular cylindrical shape including a hollow interior having a 360° curvature formed between opposing openings on end surfaces of the tubular cylindrical shape, or
wherein the semi-rigid material is structured to have a half tubular cylindrical shape including a curved inner surface and a curved outer surface each having a 180° curvature between opposing ends of the half tubular cylindrical shape.

13. The acoustic coupling article of claim 1, wherein the semi-rigid material is configurable to a flat rectangular shape, or to a tubular cylindrical shape in which opposing ends are coupled and include a gap between the opposing ends.

14. The acoustic coupling article of claim 13, further comprising an attachment component to couple the opposing ends.

15. The acoustic coupling article of claim 1, wherein the semi-rigid material is able to be molded to match a three-dimensional polygon shape of the receiving body.

16. The acoustic coupling article of claim 1, wherein the acoustic coupling article is included in a system for use in tomographic ultrasound imaging, expanded effective synthetic aperture ultrasound imaging, therapeutic ultrasound, or a combination thereof.

17. The acoustic coupling article of claim 1, wherein the receiving body includes an anatomical structure of a living subject including an abdomen, a thorax, a neck including a throat, an arm, a leg, a knee joint, a hip joint, an ankle joint, an elbow joint, a shoulder joint, a wrist joint, a breast, a genital, or a head including a cranium.

18. The acoustic coupling article of claim 1, wherein the at least one bracket component is removably attachable to a housing body that houses the array of acoustic signal transducer elements.

19. The acoustic coupling article of claim 1, wherein the semi-rigid material has a thickness in a range of 1 cm to 12 cm.

* * * * *

UNITED STATES PATENT AND TRADEMARK OFFICE
CERTIFICATE OF CORRECTION

PATENT NO. : 11,191,521 B2
APPLICATION NO. : 16/294847
DATED : December 7, 2021
INVENTOR(S) : Evan Freiburg et al.

It is certified that error appears in the above-identified patent and that said Letters Patent is hereby corrected as shown below:

In the Specification

In Column 9, Line 11, delete "an" and insert -- can --.

In Column 17, Line 59, delete "In a" and insert -- In --.

In Column 18, Line 56, delete "105B'" and insert -- 505B' --.

In Column 18, Line 60, delete "105B'" and insert -- 505B' --.

In Column 18, Line 62, delete "105E'," and insert -- 505E', --.

In Column 18, Line 66, delete "105E'," and insert -- 505E', --.

In Column 19, Line 4, delete "105E'," and insert -- 505E', --.

In the Claims

In Column 22, Line 3, in Claim 1, delete "dB/MHz-cm" and insert -- dB/MHz·cm --.

In Column 22, Line 55, in Claim 8, after "article" delete "medium".

Signed and Sealed this
Seventeenth Day of May, 2022

Katherine Kelly Vidal
*Director of the United States Patent and Trademark Office*